(12) United States Patent
Manstrom et al.

(10) Patent No.: US 8,485,985 B2
(45) Date of Patent: Jul. 16, 2013

(54) PHYSIOLOGICAL SENSOR DELIVERY DEVICE AND METHOD

(75) Inventors: Dale R. Manstrom, Shakopee, MN (US); Amy R. Raatikka, Plymouth, MN (US); Robert F. Wilson, Roseville, MN (US); Edward R. Miller, Eden Prairie, MN (US); Jung Kwon Pak, Plymouth, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 0 days.

(21) Appl. No.: 13/350,158

(22) Filed: Jan. 13, 2012

(65) Prior Publication Data

US 2012/0136244 A1 May 31, 2012

Related U.S. Application Data

(63) Continuation of application No. 12/557,685, filed on Sep. 11, 2009, now Pat. No. 8,298,156.

(60) Provisional application No. 61/096,216, filed on Sep. 11, 2008.

(51) Int. Cl.
*A61B 5/00* (2006.01)

(52) U.S. Cl.
USPC .......................................................... 600/561

(58) Field of Classification Search
USPC .......................................................... 600/561
See application file for complete search history.

(56) References Cited

U.S. PATENT DOCUMENTS 4,771,782 A * 9/1988 Millar ........................... 600/486
4,850,358 A * 7/1989 Millar ........................... 600/486

(Continued)

FOREIGN PATENT DOCUMENTS

CN   1829466 A    9/2006
EP   01419796 B1  3/2008

(Continued)

OTHER PUBLICATIONS

FISO Technologies, Inc., Brochure (Product Data Sheet) for "FOP-MIV Pressure Sensor," downloaded from http://www.fiso.com on Aug. 29, 2008, 2 pages, Quebec, Canada.

(Continued)

*Primary Examiner* — Max Hindenburg
(74) *Attorney, Agent, or Firm* — Fredrikson & Byron, P.A.

(57) ABSTRACT

An intravascular sensor delivery device for measuring a physiological parameter of a patient, such as blood pressure, within a vascular structure or passage. In some embodiments, the device can be used to measure the pressure gradient across a stenotic lesion or heart valve. For example, such a device may be used to measure fractional flow reserve (FFR) across a stenotic lesion in order to assess the severity of the lesion. The sensor delivery device has a distal sleeve configured to pass or slide over a standard medical guidewire. Some distance back from the sensor and distal sleeve, the device separates from the guidewire to permit independent control of the sensor delivery device and the guidewire. The sensor delivery device can be sized to pass over different sizes of guidewires to enable usage in coronary and peripheral arteries, for example. The sensing mechanism (sensor) can be a fiber optic pressure sensor, such as a MEMS-based Fabry-Perot fiber optic pressure sensor, for example, or could employ some other technology, e.g., MEMS capacitive or piezoresistive sensor.

15 Claims, 21 Drawing Sheets

U.S. PATENT DOCUMENTS

| | | | | |
|---|---|---|---|---|
| 4,928,693 A * | 5/1990 | Goodin et al. | ................ | 600/434 |
| 4,966,148 A * | 10/1990 | Millar | ........................... | 600/486 |
| 4,991,590 A * | 2/1991 | Shi | ................................ | 600/480 |
| 5,046,497 A * | 9/1991 | Millar | ........................... | 600/309 |
| 5,178,159 A * | 1/1993 | Christian | ..................... | 600/585 |
| 5,280,786 A * | 1/1994 | Wlodarczyk et al. | ......... | 600/327 |
| 5,395,311 A * | 3/1995 | Andrews | ........................ | 604/22 |
| 5,533,957 A * | 7/1996 | Aldea | ............................. | 600/16 |
| 5,597,377 A * | 1/1997 | Aldea | ............................. | 600/16 |
| 5,715,827 A * | 2/1998 | Corl et al. | ..................... | 600/486 |
| 5,782,797 A * | 7/1998 | Schweich et al. | ............. | 604/507 |
| 5,938,624 A * | 8/1999 | Akerfeldt et al. | ............. | 600/585 |
| 6,112,598 A * | 9/2000 | Tenerz et al. | ................... | 73/756 |
| 6,146,354 A * | 11/2000 | Beil | ................................ | 604/28 |
| 6,166,806 A * | 12/2000 | Tjin | ................................ | 356/336 |
| 6,167,763 B1 * | 1/2001 | Tenerz et al. | ................... | 73/756 |
| 6,196,980 B1 * | 3/2001 | Akerfeldt et al. | ............. | 600/585 |
| 6,248,083 B1 * | 6/2001 | Smith et al. | .................... | 600/585 |
| 6,471,656 B1 * | 10/2002 | Shalman et al. | ............. | 600/486 |
| 6,615,667 B2 * | 9/2003 | Smith | ............................. | 73/719 |
| 6,852,261 B2 * | 2/2005 | Benjamin | ..................... | 264/248 |
| 6,868,736 B2 * | 3/2005 | Sawatari et al. | ................ | 73/800 |
| 6,976,965 B2 * | 12/2005 | Corl et al. | ..................... | 600/486 |
| 7,134,994 B2 * | 11/2006 | Alpert et al. | ................... | 600/300 |
| 7,329,223 B1 * | 2/2008 | Ainsworth et al. | ........... | 600/300 |
| 2004/0168519 A1 * | 9/2004 | Kalvensten et al. | ............ | 73/727 |
| 2005/0065511 A1 | 3/2005 | Geistert | | |
| 2006/0133715 A1 * | 6/2006 | Belleville et al. | ............... | 385/13 |
| 2007/0255145 A1 * | 11/2007 | Smith et al. | .................... | 600/485 |
| 2008/0119758 A1 * | 5/2008 | Samuelsson et al. | ......... | 600/561 |
| 2010/0241008 A1 * | 9/2010 | Belleville et al. | ............. | 600/478 |

FOREIGN PATENT DOCUMENTS

| | | |
|---|---|---|
| RU | 1802695 A3 | 3/1993 |
| RU | 47203 U1 | 8/2005 |
| WO | WO 96/07351 A1 | 3/1996 |

OTHER PUBLICATIONS

OPSENS, Inc., Brochure (Product Data Sheet) entitled, "Fiber Optic Miniature Physiological Pressure Sensor OPP-M, MEMS-based Fiber Optic Pressure Sensor for Life Science Applications," downloaded from http://www.opsens.com on Aug. 29, 2008, 2 pages, Quebec, Canada.

Nico H.J. Piljs, M.D., PhD. et al., "Measurement of Fractional Flow Reserve to Assess the Functional Severity of Coronary-Artery Stenoses", The New England Journal of Medicine, Sep. 12, 2008, pp. 1703-1708.

Ming Li, Ming Wang and Hongpu Li, "Optical MEMS pressure sensor based on Fabry-Perot interferometry", Optics Express, Feb. 20, 2006, pp. 1497-1504.

Patrick W. Serruys, MD, PhD et al., "Intercoronary Pressure and Flow Velocity with Sensor-Tip Guidewires: A New Methodological Approach for Assessment of Coronary Hemodynamics Before and After Coronary Interventions", The American Journal of Cardiology, May 20, 1993.

Notification of Transmittal of the International Search Report and Written Opinion of the International Searching Authority for corresponding application PCT/US2009/056664, Nov. 5, 2009, 12 pgs.

Canadian Examination Report of corresponding Canadian application 2,734,698 mailed Jun. 30, 2011, 3 pgs.

Canadian Examination Report of corresponding Canadian application 2,734,698 mailed Oct. 27, 2011, 3 pgs.

Sauser, F.R. et al., Pressure microsensing catheters for neonatal care. Proceedings of IEEE Sensors, 3, 2004, pp. 1476-1479.

Tabbara M. et at., "Potential of intraluminal ultrasound for antioplasty guidance," Proceedings of SPIE—The International Society for Optical Engineering, 1201, 1990, pp. 523-526.

* cited by examiner

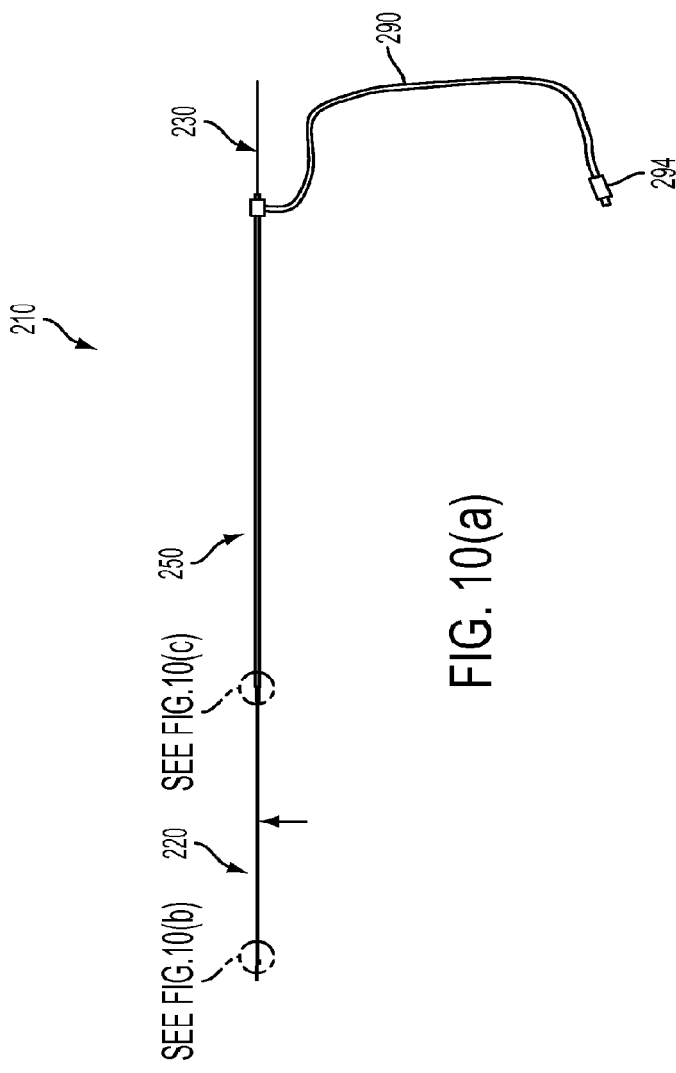
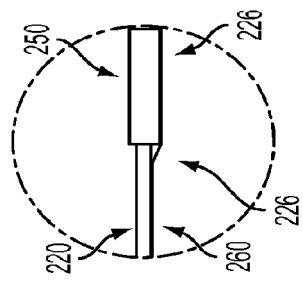
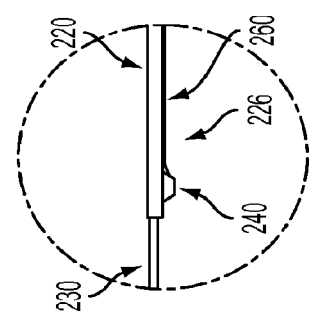
FIG. 10(a)
FIG. 10(b)
FIG. 10(c)

PHYSIOLOGICAL SENSOR DELIVERY DEVICE AND METHOD

CROSS-REFERENCE TO RELATED APPLICATIONS

This application is a continuation application of U.S. patent application Ser. No. 12/557,685, filed Sep. 11, 2009, which in turn claims priority to U.S. provisional patent application Ser. No. 61/096,216, filed Sep. 11, 2008, the contents of each of which are hereby incorporated by reference in their entirety.

TECHNICAL FIELD

This application relates generally to the field of medical device technology and, more particularly, to devices and methods for positioning and utilizing physiological sensors in anatomical (e.g., vascular) structures of patients, such as in blood vessels or across heart valves.

BACKGROUND

Certain physiological measurements may be made by positioning a sensor within a patient. Such physiological measurements may include, for example, measurements of blood parameters, such as blood pressure, oxygen saturation levels, blood pH, etc. Some such measurements may have diagnostic value and/or may form the basis for therapy decisions.

A technique for evaluating the degree to which a stenotic lesion obstructs flow through a blood vessel is called the Fractional Flow Reserve measurement (FFR). To calculate the FFR for a given stenosis, two blood pressure readings are taken. One pressure reading is taken on the distal side of the stenosis (e.g., downstream from the stenosis), the other pressure reading is taken on the proximal side of the stenosis (e.g., upstream from the stenosis, towards the aorta). The FFR is defined as the ratio of maximal blood flow in a stenotic artery, taken distal to the lesion, to normal maximal flow, and is typically calculated based on a measured pressure gradient of the distal pressure to the proximal pressure. The FFR is therefore a unitless ratio of the distal and proximal pressures. The pressure gradient, or pressure drop, across a stenotic lesion is an indicator of the severity of the stenosis, and the FFR is a useful tool in assessing the pressure drop. The more restrictive the stenosis is, the greater the pressure drop, and the lower the resulting FFR. The FFR measurement may be a useful diagnostic tool. For example, clinical studies have shown that an FFR of less than about 0.75 may be a useful criterion on which to base certain therapy decisions. Pijls, DeBruyne et al., *Measurement of Fractional Flow Reserve to Assess the Functional Severity of Coronary-Artery Stenoses*, 334:1703-1708, New England Journal of Medicine, Jun. 27, 1996. A physician might decide, for example, to perform an interventional procedure (e.g., angioplasty or stent placement) when the FFR for a given stenotic lesion is below 0.75, and may decide to forego such treatment for lesions where the FFR is above 0.75. Thus, the FFR measurement could become a decision point for guiding treatment decisions.

One method of measuring the pressure gradient across a lesion is to use a small catheter connected to a blood pressure measurement sensor. The catheter would be passed over the guidewire which has already been placed across the lesion. The catheter would be advanced down the guidewire until the tip of the catheter crosses the lesion. The blood pressure on the distal side of the lesion is recorded. This pressure would be divided by the pressure value recorded in the aorta. A disadvantage of using this method is that some error may be introduced due to the cross sectional size of the catheter. As the catheter crosses the lesion, the catheter itself introduces blockage, in addition to that caused by the lesion itself. The measured distal pressure would therefore be somewhat lower than it would be without the additional flow obstruction, which may exaggerate the measured pressure gradient across the lesion.

Pressure drop can also be measured across a heart valve. When a heart valve is regurgitant, a less than optimal pressure drop is typically observed. Using a catheter to measure pressure drop is common across a heart valve. However, because of the catheter size, the heart valve may not seal well around the catheter. Leakage might also result from the presence of the catheter and may contribute to an inaccurate pressure drop reading. One example of where this could occur is in the mitral valve (e.g., mitral valve regurgitation).

One method of measuring blood pressure in a patient is to use a pressure sensing guidewire. Such a device has a pressure sensor embedded within the guidewire itself. A pressure sensing guidewire could be used in the deployment of interventional devices such as angioplasty balloons or stents. Prior to the intervention, the pressure sensing guidewire would be deployed across a stenotic lesion so the sensing element is on the distal side of the lesion and the distal blood pressure is recorded. The guidewire may then be retracted so the sensing element is on the proximal side of the lesion. The pressure gradient across the stenosis and the resulting FFR value could then be calculated.

To use a guidewire-based pressure sensor in certain applications, the guidewire must be repositioned so the sensing element of the guidewire is correctly placed with respect to a stenotic lesion, for example. Blood pressure measurements for calculating FFR, for example, are generally taken on both sides of a given stenosis, so the guidewire is typically retracted across the stenosis to make the upstream measurement. After retracting the guidewire to make the proximal pressure measurement (aortic pressure or upstream coronary pressure), the guidewire may again be repositioned downstream of the lesion, for example, if it is determined (e.g., based on the FFR calculation) that an interventional device should be deployed. In cases where there are multiple lesions, the sensing element of a pressure sensing guidewire would need to be advanced and retracted across multiple lesions, and would potentially have to be advanced and repositioned again for each such lesion. Advancing and maneuvering a pressure sensing guidewire though stenotic lesions and the vasculature, for example, can be a difficult and/or time consuming task.

Physician preference is another factor that may influence the choice of diagnostic tools or techniques used for certain applications. For example, some physicians may tend to become accustomed to using certain specific guidewires for certain applications. "Standard" (e.g., commercially available) medical guidewires may vary in size, flexibility, and torque characteristics. A physician may prefer to use different guidewires for different tasks, for example, to access hard-to-reach anatomical areas, or when encountering bifurcations in arteries. Certain guidewires may therefore be better suited for specific tasks because of the torque and flexing characteristics, and a physician may display a strong preference for using a certain guidewire based on the specific task (or tasks) he or she is facing. A pressure sensing guidewire may have torque and flexing characteristics that are either unknown to the physician, or that are unsuitable for a particular task, because such a guidewire is specifically constructed to have a pressure sensor incorporated as part of the guidewire itself. As a result, a physician may find it difficult to maneuver a pressure sensing guidewire into an anatomical location of interest, as compared to a "standard" (e.g., non-pressure sensing) medical guidewire.

Having grown accustomed to the handling characteristics of a particular non-pressure sensing guidewire, a physician may be reluctant to employ a pressure sensing guidewire, which may increase the time and difficulty of positioning and repositioning the pressure sensing guidewire across a stenotic lesion, for example. In such cases, a physician may choose to forego the benefit of a diagnostic measurement, such as FFR, and simply choose to deploy some form of interventional therapy as a conservative approach to such decisions. If the diagnostic measurement techniques and the associated devices were simple enough to use, more physicians would use them and thereby make better therapy decisions.

SUMMARY

Physiological sensor delivery devices and methods according to embodiments of the invention may be used in diagnostic applications, such as cardiovascular procedures in coronary arteries, interventional radiology applications in peripheral arteries, and structural heart applications in heart valves.

An intravascular sensor delivery device according to some embodiments of the invention comprises a distal sleeve with a guidewire lumen for sliding over a medical guidewire, a sensor coupled to the distal sleeve, the sensor adapted to measure a physiological parameter of a patient and generate a signal representative of the physiological parameter. A proximal portion is coupled to the distal sleeve. The proximal portion comprises a communication channel for communicating the signal from the sensor to a location outside of the patient (such as a display monitor, or another medical device, etc.). The proximal portion of the sensor delivery device is adapted to facilitate positioning of the sensor within a vascular structure of the patient.

A method of assessing the severity of a stenotic lesion in a blood vessel of a patient according to some embodiments of the invention comprises deploying an intravascular sensor delivery device over a guidewire to a position such that the sensor is distal to the lesion, and measuring a distal pressure. In some embodiments, the method may next comprise using the sensor delivery device to move the sensor to a position proximal of the lesion and measuring proximal (e.g., aortic) pressure, then calculating a ratio (or some other quantitative comparison) of the two pressure measurements. In some embodiments, the proximal pressure may be obtained from a separate pressure sensing apparatus (e.g., a pressure sensor connected to a fluid injection system), and the distal and proximal pressure measurements may be made substantially simultaneously (e.g., to reduce timing errors, etc.) before making a quantitative comparison of the two values.

BRIEF DESCRIPTION OF THE DRAWINGS

FIG. 10 is a side view of a sensor delivery device having an over-the-wire configuration according to one embodiment of the invention;

DETAILED DESCRIPTION

The following detailed description should be read with reference to the accompanying drawings, in which like numerals denote like elements. The drawings, which are not necessarily to scale, depict selected embodiments of the invention—other possible embodiments may become readily apparent to those of ordinary skill in the art with the benefit of these teachings. Thus, the embodiments shown in the accompanying drawings and described below are provided for illustrative purposes, and are not intended to limit the scope of the invention as defined in the claims appended hereto.

Figure 1:
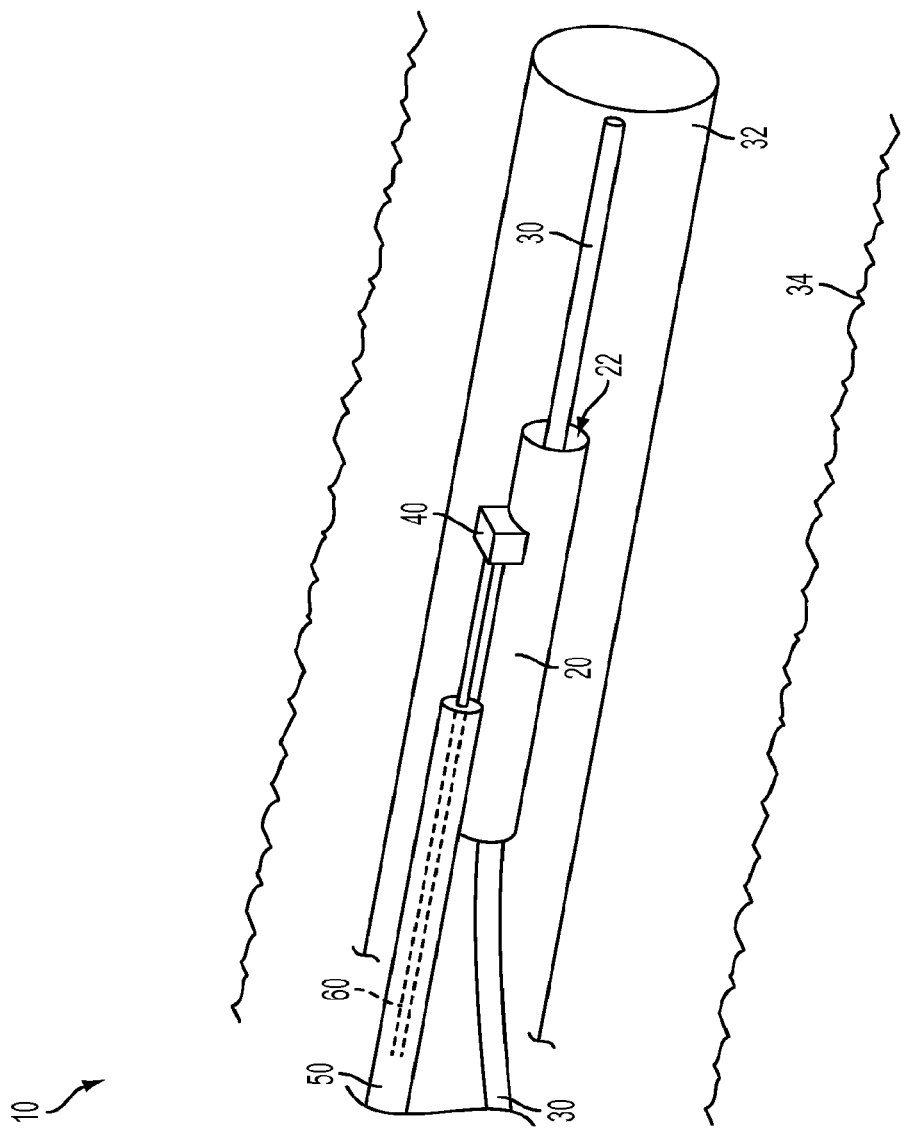
FIG. 1 is a perspective view of a sensor delivery device according to an embodiment of the invention.

An example of a sensor delivery device according to certain embodiments of the invention is shown in FIG. 1. The sensor delivery device 10 of FIG. 1 includes a distal sleeve 20 having a guidewire lumen 22 for slidably receiving a medical guidewire 30. A sensor 40 is coupled to the distal sleeve 20, sensor 40 being capable of sensing and/or measuring a physiological parameter of a patient and generating a signal representative of the physiological parameter. Thus, the distal sleeve 20, and hence, the sensor 40, may be positioned within a patient (e.g., within an anatomical structure of a patient, such as within a vein, artery, or other blood vessel, or across a heart valve, for example) by causing the distal sleeve 20 to slide over the medical guidewire 30 to the desired position.

The sensor delivery device 10 of FIG. 1 also includes a proximal portion 50, which is coupled to the distal sleeve 20. The proximal portion 50 includes a communication channel 60 for communicating the signal from the sensor 40 to a location outside of the patient (e.g., to a processor, display, computer, monitor, or to another medical device). Communication channel 60 may comprise a fiber optic communication channel in certain preferred embodiments, such as where the sensor 40 is a fiber optic pressure sensor. Alternately, communication channel 60 may comprise an electrically conductive medium, such as one or more electrical conducting wires. Of course, many other forms of communication media may be suitable for transmitting the signal generated by sensor 40 to a location outside of the patient. In some embodiments of the invention, the communication channel 60 may comprise any of a variety of fluid and/or non-fluid communication media, such as a wireless communication link, or an infrared capability, or acoustic communications such as ultrasound, as possible examples.

The proximal portion 50 is also adapted to assist an operator (e.g., a physician or other medical staff) in positioning the distal sleeve 20 and the sensor 40 within an anatomical (e.g., vascular) structure of the patient. This is typically accomplished by an operator first inserting a "standard" medical guidewire 30 into a patient's vasculature and advancing it past an area of interest. The sensor delivery device 10 is then deployed by "threading" the distal sleeve 20 onto the guidewire 30 such that the lumen 22 slides over the guidewire 30, and advancing the distal sleeve 20 (and the associated sensor 40) by moving (e.g., pushing and/or pulling) the proximal portion 50 until sensor 40 is in the desired location.

The device 10 and the guidewire 30 are typically manipulated inside a guiding catheter 32, which has been placed in the anatomical (e.g., vascular) structure of interest. In certain preferred embodiments of the invention, the guidewire lumen 22 may be sized to slide over "standard" sized medical guidewires. For example, a number of manufacturers make medical guidewires that range in size from less than about 0.014 inches outer diameter to more than about 0.038 inches outer diameter, typically having a finite number of common sizes within this range. "Standard" size medical guidewires might, for example, have outer diameters of 0.010, 0.014, 0.018, 0.021, 0.025, 0.028, 0.032, 0.035, and 0.038 inches. Thus, in certain preferred embodiments of the invention, the guidewire lumen 22 may be sized appropriately to slide over a particular standard size medical guidewire. A device according to preferred embodiments of the invention may therefore be made available in a range of sizes corresponding to standard medical guidewire sizes.

One potential advantage of a sensor delivery device 10 according to embodiments of the invention is that it allows a physician to use the guidewire of their choice. Sensor delivery device 10 can be sized to be used with any guidewire. The physician may, for example, choose a particular guidewire based on its unique flexing and torque characteristics for certain procedures. Delivery device 10 according to various embodiments of the invention provides the physician with the ability to use whichever guidewire is deemed best suited for the particular application.

Another potential advantage of the sensor delivery device 10 is that it does not require repositioning of the guidewire in order to make sensor readings. Once the guidewire has been positioned across a stenotic lesion, for example, the sensor delivery device 10 can be positioned (e.g., advanced and/or retracted) over the guidewire and the sensor 40 can therefore be advanced and refracted across lesions to make pressure readings, for example, without moving the guidewire. A physician may also save time by not having to reposition the guidewire across the lesion or lesions to make such measurements.

In the example shown in FIG. 1, the device 10 is being deployed using guiding catheter 32, which has been placed within a vascular structure of interest (in this example, blood vessel 34, which could be, for example, a coronary artery of the patient). In certain embodiments of the invention, the size or "footprint" (e.g., the width and/or the cross-sectional area) of device 10 may allow it to fit within certain standard sized guiding catheters. For example, in certain diagnostic applications, it would be desirable to have device 10 deployed within a certain sized guiding catheter (e.g., smaller than about 4 or 5 French (FR)).

In certain embodiments of the invention, the distal sleeve 20 of the device may be substantially concentric with the guidewire 30. The coupling of the proximal portion 50 to the distal sleeve 20 allows the guidewire 30 to separate from the rest of device 10 (e.g., in what is sometimes referred to as a "monorail" catheter configuration); this would typically occur inside the guiding catheter 32. The guidewire 30 and device 10 would both exit the patient at the proximal end of the guiding catheter 32 as separate devices. Having the device 10 and guidewire 30 separate allows the physician to independently control device 10 and guidewire 30, as necessary. It may also allow a physician to use a shorter guidewire for catheter exchange. For example, a monorail-type configuration may allow for the use of a guidewire that is approximately 170 to 200 cm long, whereas an "over-the-wire" configuration might require the use of a much longer (e.g., up to 300 cm or more) guidewire. Having the device 10 and guidewire 30 separate (except at the distal sleeve 20) may also result in less friction (e.g., within the guiding catheter 32) than if the device 10 and guidewire 30 had to be moved together as a unit. In some embodiments, a hydrophilic coating may be applied to various portions of the device to further reduce the amount of friction encountered, for example, when advancing or retracting device 10.

One diagnostic application in which various embodiments of the invention may be well-suited is the measurement of Fractional Flow Reserve (FFR). As noted above, the FFR measurement quantifies the degree to which a stenotic lesion, for example, obstructs flow through a blood vessel. To calculate the FFR for a given stenosis, two blood pressure measurements are needed: one pressure reading is taken on the distal side of the stenosis (downstream side), the other pressure reading is taken on the proximal side of the stenosis (upstream side). The FFR is therefore a unitless ratio of the distal pressure to the proximal pressure. The pressure gradient across a stenotic lesion is an indicator of the severity of the stenosis. The more restrictive the stenosis is, the more the pressure drop, and the lower the FFR.

To add clarity and context to the disclosure, several embodiments of the invention will now be described below in the context of making FFR measurements. However, it should be realized that there are other applications in which physiological parameter measurements could be facilitated with the devices and/or methods described herein.

Figure 2:
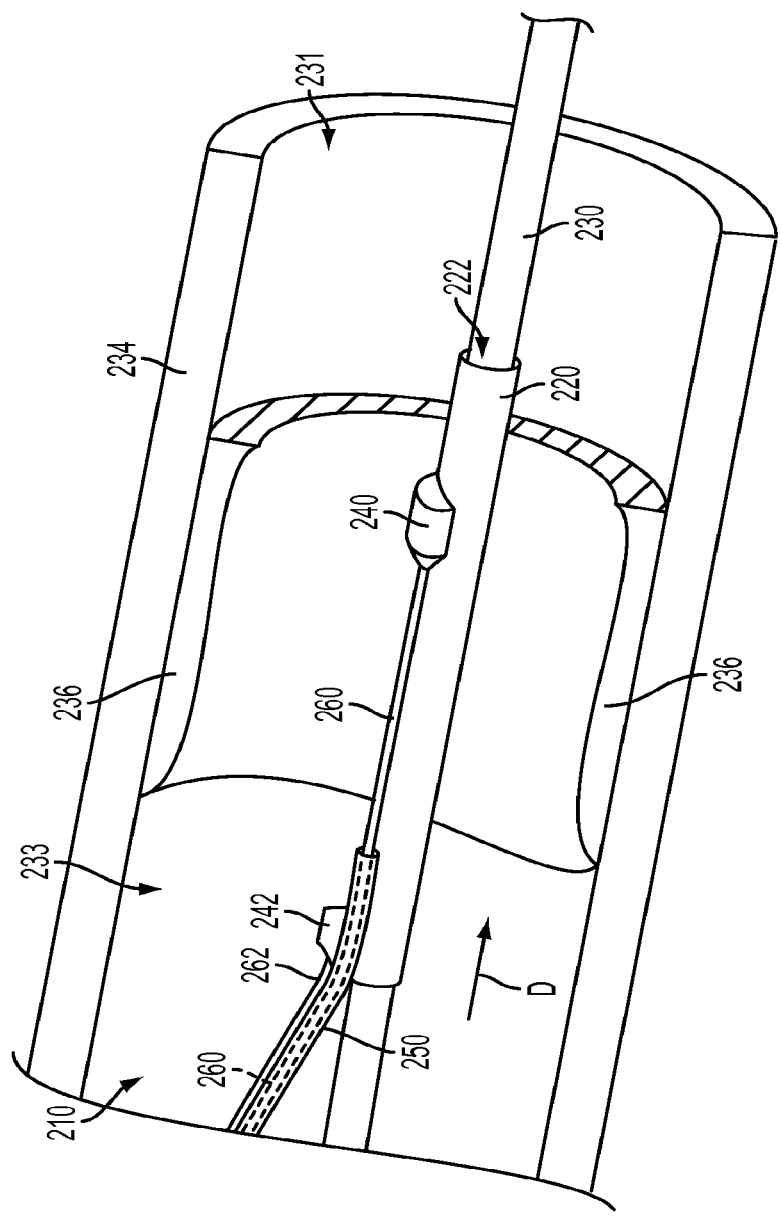
FIG. 2 is a conceptual perspective view of a sensor delivery device for making physiological measurements according to an embodiment of the invention.

FIG. 2 is a perspective view of a sensor delivery device for measuring a physiological parameter in a patient according to an embodiment of the invention. The embodiment shown in FIG. 2 might, for example, be deployed to make an FFR measurement in a blood vessel of a patient. FIG. 2 shows a sensor delivery device 210 being deployed in a blood vessel of a patient (e.g., coronary artery 234) across a stenosis (e.g., stenotic lesion 236). To make an FFR measurement, for example, first sensor 240 may be positioned to measure distal (downstream) blood pressure, $P_d$, at a location 231 downstream of a location of interest (e.g., stenotic lesion 236). First sensor 240 may then be positioned to measure proximal (upstream) blood pressure, $P_p$, at a location 233 upstream of a location of interest (e.g., stenotic lesion 236). FFR is simply calculated as the ratio of distal pressure to proximal pressure, or FFR=$(P_d/P_p)$. The use of the terms "downstream" and "upstream" are with respect to the normal direction of blood flow, "D," as shown in FIG. 2.

In FIG. 2, first sensor 240 is coupled to distal sleeve 220. In the embodiment shown in FIG. 2, first sensor 240 is coupled to an outer surface of distal sleeve 220. The first sensor 240 is adapted to measure a physiological parameter of a patient, such as a blood parameter (e.g., blood pressure, temperature, pH, blood oxygen saturation levels, etc.), and generate a signal representative of the physiological parameter. In certain preferred embodiments of the invention, the first sensor 240 is a fiber optic pressure sensor adapted to measure blood pressure. An example of a fiber optic pressure sensor is a Fabry-Perot fiber optic pressure sensor, which is a commercially available sensor. Examples of Fabry-Perot fiber optic sensors are the "OPP-M" MEMS-based fiber optic pressure sensor (400 micron size) manufactured by Opsens (Quebec, Canada), and the "FOP-MIV" sensor (515 micron size) manufactured by Fiso Technologies, Inc. (Quebec, Canada). In certain alternate embodiments, first sensor 240 may be a piezo-resistive pressure sensor (e.g., a MEMS piezo-resistive pressure sensor), and in other embodiments, first sensor 240 may be a capacitive pressure sensor (e.g., a MEMS capacitive pressure sensor). A pressure sensing range from about −50 mm Hg to about +300 mm Hg (relative to atmospheric pressure) is desired for making most physiological measurements with sensor 240, for example.

In embodiments of the invention using the Fabry-Perot fiber optic pressure sensor as the sensor 240, such a sensor works by having a reflective diaphragm that varies a cavity length measurement according to the pressure against the diaphragm. Coherent light from a light source travels down the fiber and crosses a small cavity at the sensor end. The reflective diaphragm reflects a portion of the light signal back into the fiber. The reflected light travels back through the fiber to a detector at the light source end of the fiber. The two light waves, the source light and reflected light travel in opposite directions and interfere with each other. The amount of interference will vary depending on the cavity length. The cavity length will change as the diaphragm deflects under pressure. The amount of interference is registered by a fringe pattern detector.

FIG. 2 shows proximal portion 250 coupled to the distal sleeve 220. The proximal portion 250 includes a communication channel 260 for communicating the physiological signal from the sensor 240 to a location outside of the patient (e.g., to a processor, display, computer, monitor, or to another medical device). The proximal portion 250 may preferably be formed of a material of sufficient stiffness in order to assist an operator (e.g., a physician or other medical staff) in positioning the distal sleeve 220 and the sensor 240 within a anatomical (e.g., vascular) structure of the patient.

One suitable material for the proximal portion 250 may be a stainless steel hypotube, for example. Depending on the application, the proximal portion 250 (sometimes also referred to as the "delivery tube") should typically be stiffer and more rigid than the distal sleeve 220 in order to provide a reasonable amount of control to push, pull and otherwise maneuver the device to a physiological location of interest within the patient. In interventional cardiology procedures, for example, at least a portion of the proximal portion 250 will be maneuvered within a guiding catheter positioned within the aortic artery. The proximal portion 250 in such an application should therefore be flexible enough to accommodate the arch of the aorta, while being rigid enough to push and pull the device. Accordingly, suitable materials for proximal portion 250 may also include (in addition to the aforementioned stainless steel hypotube) materials such as nitinol, nylon, and plastic, for example, or composites of multiple materials.

The communication channel 260 may be disposed along an outer surface of proximal portion 250, or may be formed within the proximal portion 250, as shown in FIG. 2. For example, communication channel 260 may comprise a communication lumen that extends longitudinally through proximal portion 250 in some embodiments. Communication channel 260 may comprise a fiber optic communication channel in certain embodiments, such as where the sensor 240 is a fiber optic pressure sensor. Alternately, communication channel 260 may comprise an electrically conductive medium, such as electrical conducting wires, or other communication media suitable for transmitting the signal generated by sensor 240. In preferred embodiments of the invention, the communication channel 260 comprises a non-fluid communication medium. In the embodiment shown in FIG. 2, communication channel 260 (e.g., a fiber optic cable) extends distally beyond proximal portion 250 and is coupled to sensor 240. The communication channel 260 in such an embodiment is at least partially housed within a communication lumen of the proximal portion 250 (e.g., a stainless steel hypotube).

FIG. 2 also shows an optional embodiment of the invention in which a second sensor 242 may be coupled to the device 210. For example, a second sensor 242 may be coupled to proximal portion 250 such that the first and second sensor 240, 242 are spaced apart sufficiently (e.g., a fixed distance apart) to span a stenotic lesion. This embodiment may offer the ability to measure FFR without having to reposition device 210, since first sensor 240 could be placed distal of the stenotic lesion 236 to measure $P_d$, and second sensor 242 could be placed proximal of the stenotic lesion 236 to measure $P_p$. Second sensor 242 may have a communication channel 262, which could be housed within proximal portion 250, or could be disposed along an outside surface of proximal portion 250, as shown in FIG. 2, for example. Further, the ability to measure $P_d$ and $P_p$ substantially simultaneously may improve accuracy and/or reduce the effects of certain types of errors illustrated and described below with reference to FIG. 3.

It should be noted that certain embodiments could have more than 2 sensors, and that the spacing between adjacent sensors in such embodiments may be varied to provide a variable spacing capability. In certain alternate embodiments of the invention, one or more sensors could be disposed on the proximal portion 250 with no sensors disposed on the distal sleeve 220, for example. In some alternate embodiments, it may be desirable to have a plurality of sensors (two, or three, or four, or more sensors) spaced at known, fixed distances, disposed along the proximal portion 250. This could, for example, provide the ability to measure $P_d$ and $P_p$ substantially simultaneously, regardless of lesion length, by selecting an appropriate pair of sensors (from among the plurality of sensors) placed across the lesion from which to obtain the $P_d$ and $P_p$ signals. Further, the sensors could have some form of radiopaque markings incorporated thereon (e.g., marker bands), which could provide a visual estimate of lesion size in conjunction with the measurement of physiological parameters (e.g., $P_d$ and $P_p$).

Figure 3:
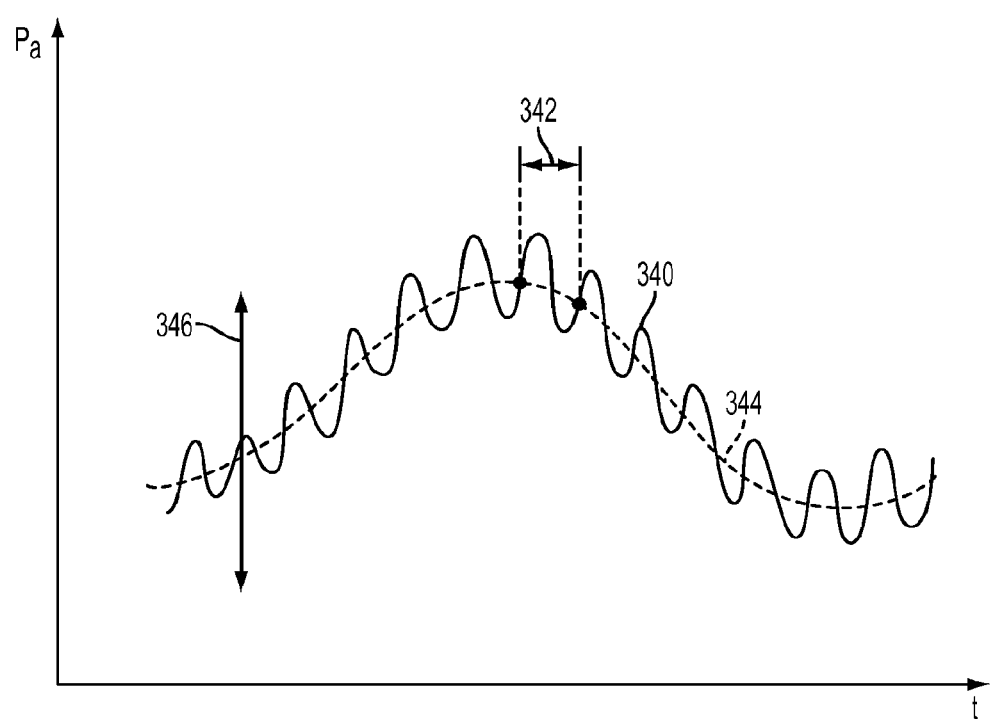
FIG. 3 is an conceptual plot of a patient's blood pressure as a function of time.

FIG. 3 graphically illustrates several possible sources of error in measuring blood pressure, particularly as they may affect the calculation of FFR, for example. FIG. 3 is a conceptual plot of blood pressure, 340, as a function of time for a given patient, P(t). One potential error in calculating FFR is due to the fluctuations in blood pressure due to the systolic and diastolic phases of the cardiac cycle 342. Unless $P_d$ and $P_p$ are measured at substantially the same phase of the cardiac cycle 342, there may be some amount of error introduced. Similarly, a more slowly varying source of error can also be introduced by the effect of the respiratory cycle (e.g., inspiration and expiration) on blood pressure, as illustrated at 344 in FIG. 3. A third source of error could be introduced by changes in the patient's posture, which could either raise or lower the overall pressure profile as indicated at 346 in FIG. 3. Embodiments of the invention which have the ability to measure $P_d$ and $P_p$ substantially simultaneously, such as the two-sensor embodiment shown in FIG. 2, may be able to minimize or eliminate the effects of such "timing errors" on the FFR calculation. Another method of addressing the effects of such "timing errors" will be discussed below in the context of using a contrast injection system in conjunction with a sensor delivery device, according to some embodiments of the invention.

Referring again to FIG. 2, distal sleeve 220 may be substantially tubular, as shown, or may have any shape that allows distal sleeve 220 to slide over a medical guidewire 230 in a anatomical (e.g., vascular) structure of interest. In the context of measuring FFR in a coronary artery, for example, it may be desirable that distal sleeve 220 be substantially cylindrical in cross-section to minimize the total cross-sectional area of the device. Distal sleeve 220 may be preferably formed of a flexible material in some embodiments to facilitate positioning and placement of the distal sleeve 220 (and sensor 240) over a guidewire 230 through narrow vascular structures such as coronary arteries. In certain preferred embodiments, the distal sleeve 220 comprises a flexible polyimide tube sized for placement in anatomical (e.g., vascular) structures of interest, such as in coronary arteries or peripheral arteries. In some embodiments, the distal sleeve 220 may comprise a flexible microcoil tube. In some embodiments, flexibility may be achieved and/or enhanced by applying a series of cuts along the surface of the tube. For example, a plurality of cuts or notches along a length of the outer surface of distal sleeve 220 may be applied (e.g., by laser cutting techniques known to those of ordinary skill in this field). Such cuts or notches may be substantially circumferentially directed, and may extend at least partially around the circumference of the distal sleeve. Successive cuts may be angularly offset from each other to provide flexibility in all directions according to some embodiments.

The length of distal sleeve 220 may vary. In embodiments to be used in coronary arteries, for example, distal sleeve 220 may be up to about 15 inches long, and in some preferred embodiments may be 11 inches long (e.g., to facilitate use deep within certain coronary arteries). In some embodiments, the distal sleeve 220 may also include a thin covering to provide additional structural support and/or improve handling characteristics of the device. Such a covering may comprise, for example, polyester (PET) shrink tubing that substantially covers the distal sleeve.

Distal sleeve 220 has a guidewire lumen 222 that is sized to slidably receive a guidewire 230 having an outer diameter between about 0.010 inches and 0.050 inches. For making an FFR measurement in a coronary artery 234, for example, the guidewire 230 may preferably have an outer diameter of 0.014 inches, and guidewire lumen 222 would therefore need to have an inner diameter slightly larger than this to facilitate slidable movement of the distal sleeve 220 over the guidewire 230.

Figure 4A:
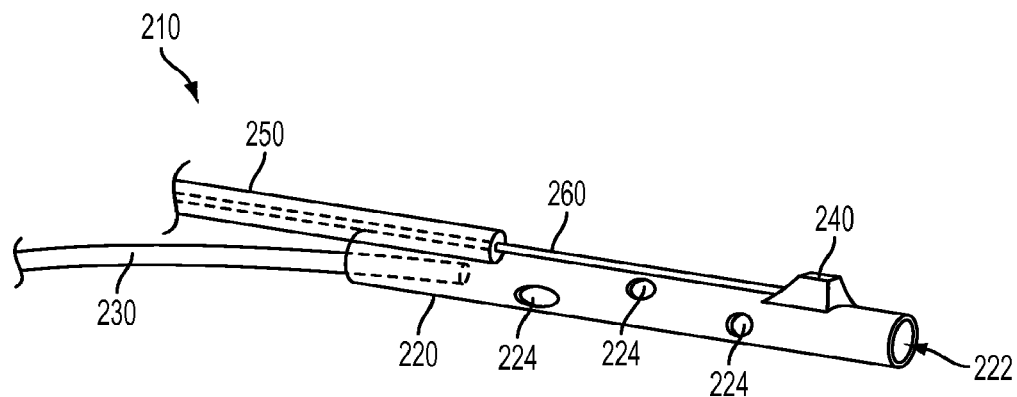
FIG. 4(a) is a side view of a sensor delivery device according to an embodiment of the invention having one or more flow holes disposed along a side portion.

FIG. 4(a) shows an embodiment of the invention in which one or more flow holes 224 are disposed along a side portion of the distal sleeve 220 (e.g., along the length of distal sleeve 220). Flow holes 224 could allow blood to flow into the guidewire lumen 222 if an operator were to pull back (e.g., withdraw) the guidewire 230 as shown in FIG. 4(a). Such an embodiment may provide an improvement in accuracy in measuring the pressure drop across a stenosis, since the pressure drop attributable to the device itself would be lessened by decreasing the effective cross-sectional area of the device.

Figure 4B:
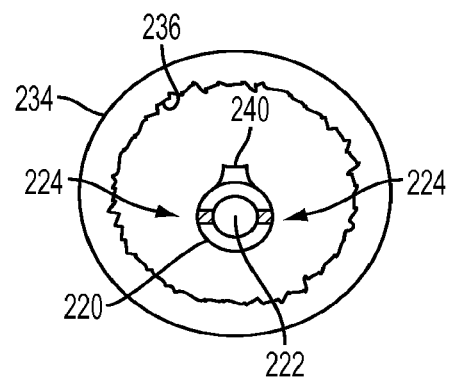
FIG. 4(b) is a cross-sectional view of a sensor delivery device according to an embodiment having one or more flow holes.

FIG. 4(b) is a cross-sectional view of an embodiment of the invention, illustrating the potential reduction in cross-sectional area that could be obtained by employing flow holes 224 in a side portion of distal sleeve 220. For example, by allowing blood to flow through flow holes 224 into guidewire lumen 222, the effective cross-sectional area of the device 210 is reduced by the area of guidewire lumen 222, and any error in blood pressure measurements caused by the flow obstruction of the device 210 itself would be accordingly reduced.

Figure 5A:
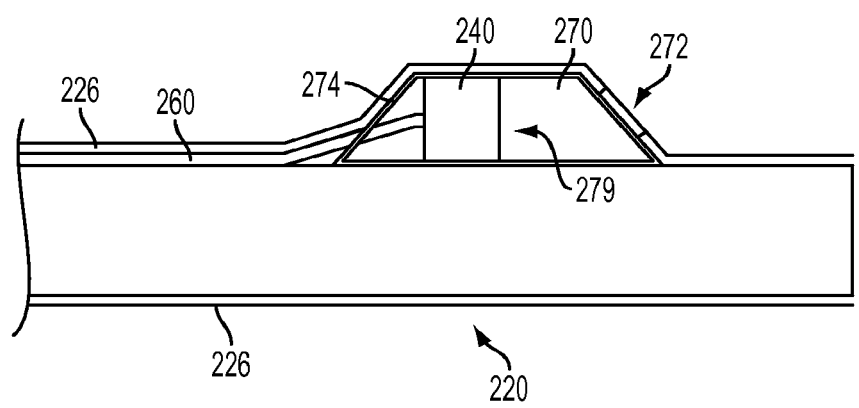
FIG. 5(a) is a cut-away side view of a sensor delivery device with a sensor housing according to one embodiment of the invention.

FIG. 5(a) is a cut-away side view of a portion of the device 210 according to certain embodiments of the invention. FIG. 5(a) shows the distal sleeve 220 and first sensor 240 of an embodiment in which sensor 240 is provided with a certain degree of protection by being at least partially covered by a sensor housing 270 disposed on distal sleeve 220. Sensor housing 270 may be substantially tubular, or may be semi-circular, or may be any other shape that provides suitable protection for sensor 240. Sensor housing 270 may be constructed of tubing such as polyimide, which is capable of being formed with a relatively thin wall thickness.

The sensor housing 270 may be constructed in several different ways, as described with reference to FIGS. 5(a) through 5(e). Fiber optic sensors, for example, may be somewhat fragile, and should typically be provided with some form of mechanical protection from stress and/or strain relief. The sensing head of sensor 240 is generally attached to the communication channel 260 (e.g., a fiber optic cable) with an adhesive. The sensing head can be prone to being pulled away from (e.g., disconnected from) the fiber optic without much force because the bonding area is typically very small. FIGS. 5(a) through 5(e) illustrate several techniques that utilize a protective sensor housing 270 surrounding the sensor 240 to minimize or eliminate the effects of such stresses on the sensor 240.

One material which may be used to construct the sensor housing 270 is a heavy metal that is x-ray visible, such as platinum. A sensor housing 270 formed of platinum may provide an x-ray marker band to facilitate the placement and positioning of the sensor 240. A platinum sensor housing 270 may be formed so it is generally thin, for example, approximately 0.001 inches in thickness. Such a thin-walled platinum sensor housing 270 may provide suitable protection to the sensor 240 from stresses that might otherwise cause it to detach from the communication channel 260.

In some embodiments, sensor housing 270 may be shaped to facilitate movement and placement of the device in the anatomical (e.g., vascular) structure of the patient. For example, as shown in FIG. 5(a), the forward and rearward portions 274 of sensor housing 270 may be formed at an angle (e.g., cut at an angle) to present a smoother, tapered structure that is easier to navigate through anatomical (e.g., vascular) structures and passages in a patient (e.g., it allows the device 210 to slide through vascular passages such as arterial walls without catching or snagging).

In some embodiments, sensor housing 270 may be formed as part of the process of forming distal sleeve 220. For example, a substantially cylindrical mandrel may be used to form a distal sleeve 220 made of a thermoset polymer (e.g., polyimide) by employing a dipping process. A slight modification of this manufacturing process could employ a "housing forming element" located alongside the mandrel at the distal end of the mandrel. A single dipping process could thereby form sensor housing 270 as an integral part of distal sleeve 220.

In some embodiments, an optional covering 226 may be applied over the sensor housing 270 and distal sleeve 220. Such a covering 226 may facilitate movement and positioning of the device 210 within a anatomical (e.g., vascular) structure of a patient. The covering 226 may also provide additional structural stability to the sensor 240, housing 270, and distal sleeve 220 arrangement. An example of a class of materials that may be suitable for forming covering 226 are thermoplastics. Such materials may sometimes be referred to as thin-walled heat-shrink tubing, and include materials such as polyolefin, fluoropolymers (PTFE), polyvinyl chloride (PVC), and polyester, specifically polyethylene terephthalate (PET). For simplicity, the term "PET tubing" will be used herein in reference to embodiments that incorporate such thin covering materials. The use of PET tubing could be employed, for example, in embodiments with or without a housing 270.

PET tubing is a heat shrink tube made from polyester that exhibits excellent tensile strength characteristics, while having a wall thickness as little as 0.0002 inches. PET tubing may be used in some embodiments of the invention to encapsulate the distal sleeve 220. This may include, for example, encapsulating the sensor housing 270 and/or a portion of the communication channel 260 (e.g., the fiber optic cable), to the extent the communication channel 260 extends from the proximal portion 250. In some embodiments, the PET tubing may also extend to cover part of the proximal portion 250, for example, where it is coupled to the distal sleeve 220. In some embodiments, PET tubing may be used to hold a fiber optic communication channel 260 in place around the distal sleeve 220. After the PET tubing has been heat shrunk, one or more openings may be cut in the PET tubing, for example, to allow an exit port for the guidewire 230.

FIG. 5(a) shows a fluid opening 272 formed in one of the portions 274 (e.g., the forward portion in this example) of the sensor housing 270. Fluid opening 272 allows fluid (e.g., blood) to enter the sensor housing 270 and come into fluid contact with sensor 240. In embodiments that incorporate a covering 226 (such as PET tubing), fluid opening 272 may be formed in the covering 226.

Figure 5B:
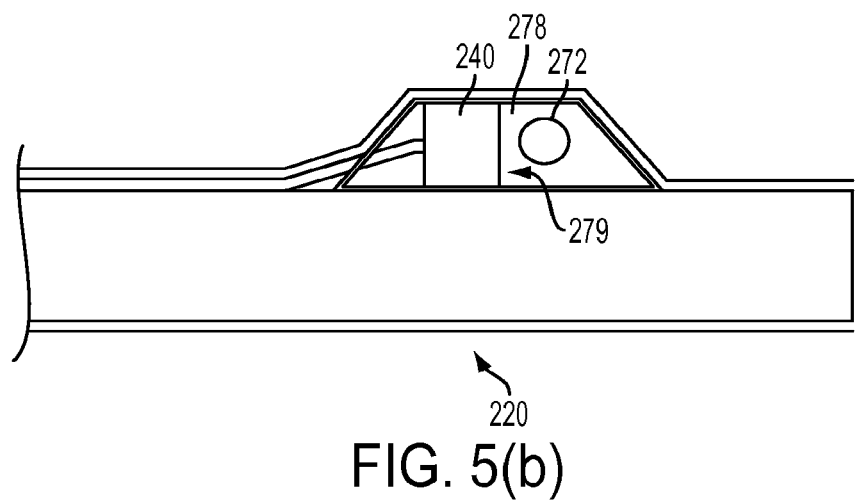
FIG. 5(b) is a cut-away side view of a sensor delivery device with a sensor housing according to one embodiment of the invention.

FIG. 5(b) shows an embodiment of the invention where the fluid opening 272 is formed in a side portion of the housing 270. This arrangement may provide a reduced likelihood of "clogging" within sensor housing 270, and/or a reduced likelihood of catching or snagging on any obstructions or bends encountered while positioning device 210. For example, plaque or calcium from arterial walls may enter the housing 270 as the device is moved through an artery; having the fluid opening 272 in a side portion of housing 270 may reduce this effect. In some embodiments, allowing the PET tubing covering 226 to remain intact at the distal end of the housing 270 may prevent foreign material from entering the housing 270 and possibly damaging the sensor 240, or affecting the accuracy of pressure measurements. After the PET tubing covering 226 has been heat shrunk over the device 210, holes can be punched through the covering 226 as needed to form fluid openings 272 to allow fluid access (e.g., blood flow) inside the sensor housing 270.

In some embodiments of the invention, the inside portion of the sensor housing 270 may be filled with a gel 278, such as a silicone dielectric gel. Silicone dielectric gels are often used with solid state sensors to protect the sensor from the effects of exposure to a fluid medium, for example. If the sensor housing 270 is filled with a gel 278 in front of the sensor diaphragm 279, then foreign material would be less likely to penetrate inside the housing 270. The gel 278 may also offer added structural stability to the sensor 240, and/or may enhance the pressure-sensing characteristics of the sensor 240. A gel 278 may be used in any of the embodiments of sensor housing 270 illustrated in FIGS. 5(a) to 5(d) and their equivalents.

Figure 5C:
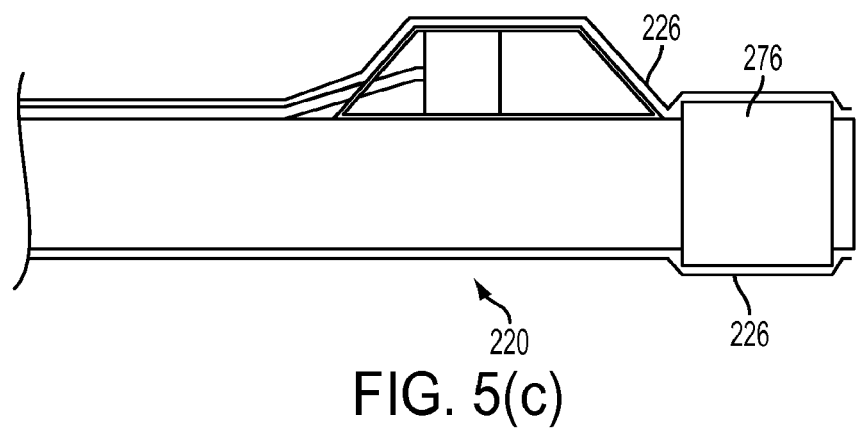
FIGS. 5(c) and 5(d) are side views of a sensor delivery device with radiopaque marker band according to certain embodiments of the invention.
Figure 5D:
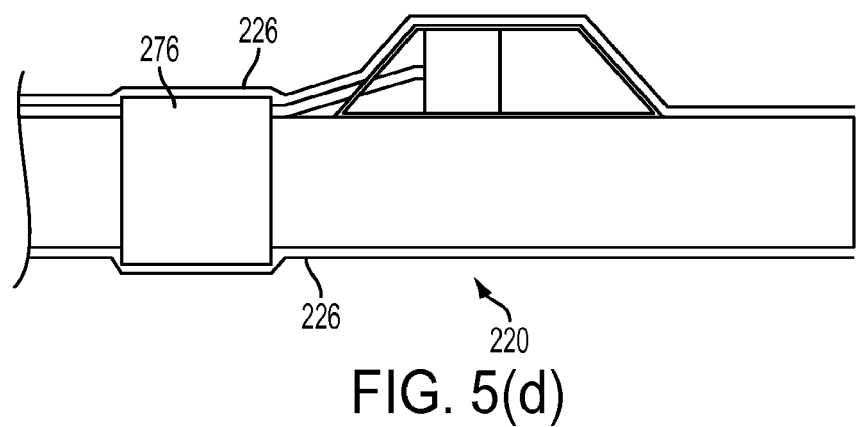

In FIGS. 5(c) and 5(d), embodiments of the invention are shown which include an optional marker band. If the sensor housing 270 is made from polyimide tubing, for example, the device 210 may not show up as well under x-ray. An optional marker band 276 could be placed near the end of the distal sleeve 220. Marker band 276 may provide a visible indication of the location of the sensor 240 when viewed under x-ray. As shown in FIG. 5(c), the marker band 276 on the end of the distal sleeve 220 may provide some structural reinforcement to the end of the distal sleeve 220. In the alternative embodiment shown in FIG. 5(d), a marker band 276 on the distal sleeve 220 located proximal of the sensor housing 270 may reduce the likelihood of the marker band 276 becoming dislodged from the device 210. In some embodiments, it may be desirable to include a number of such marker bands spaced at known distances (e.g., every 10 mm along distal sleeve 220, for example), such that the marker bands could be used to provide visual estimates of length or distance (e.g., to measure lesion length).

Figure 5E:
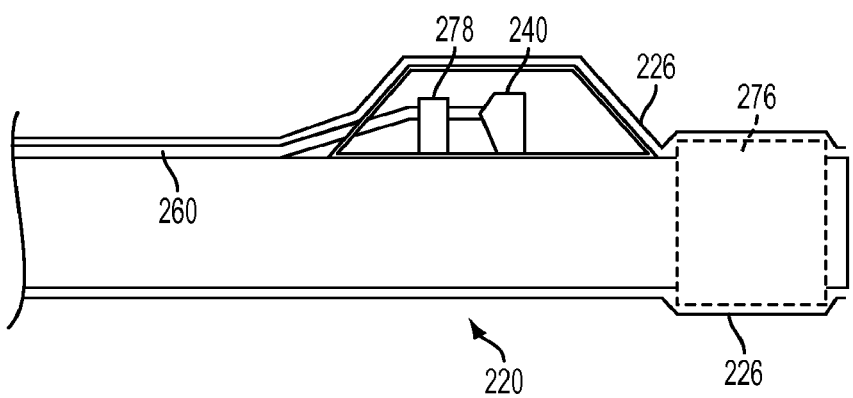
FIG. 5(e) is a cut-away side view of a sensor delivery device with a strain relief spacer according to one embodiment of the invention.

FIG. 5(e) shows an embodiment where a spacer 278 is used to provide strain relief at the connection between the sensor 240 and the communication channel 260. This strain relief may be made of any suitable material, such as polyetheretherketone (PEEK), for example. In some embodiments, spacer 278 may also be formed so as to serve as a marker band 276, substantially as described above. Spacer 278 could be employed in embodiments with a sensor housing 270, or in embodiments without a sensor housing.

Figure 6A:
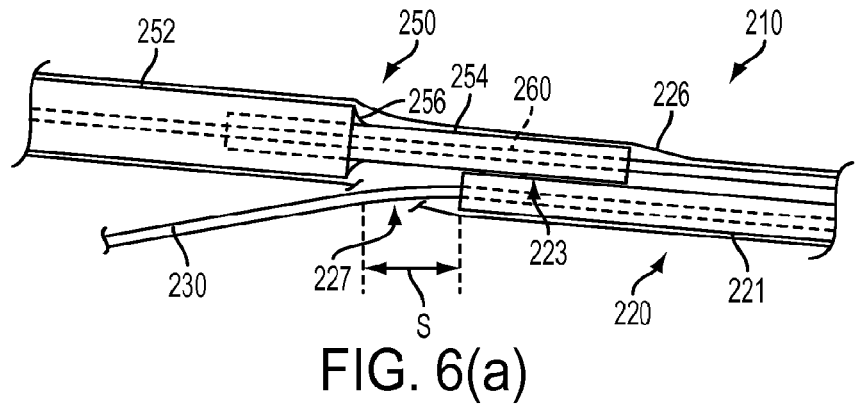
FIGS. 6(a)-6(g) are enlarged side views of a distal transition of a sensor delivery device according to certain embodiments of the invention.
Figure 6B:
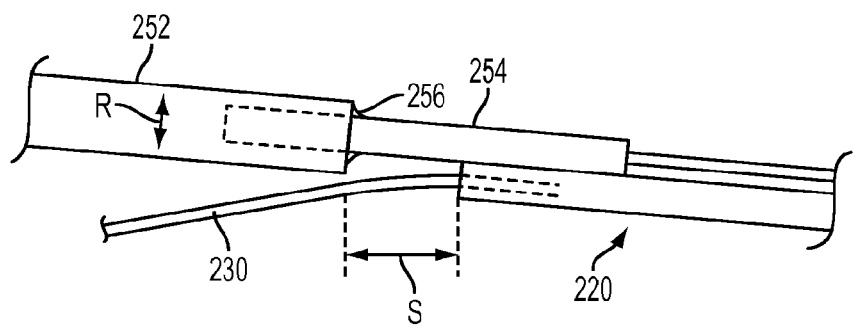
Figure 6C:
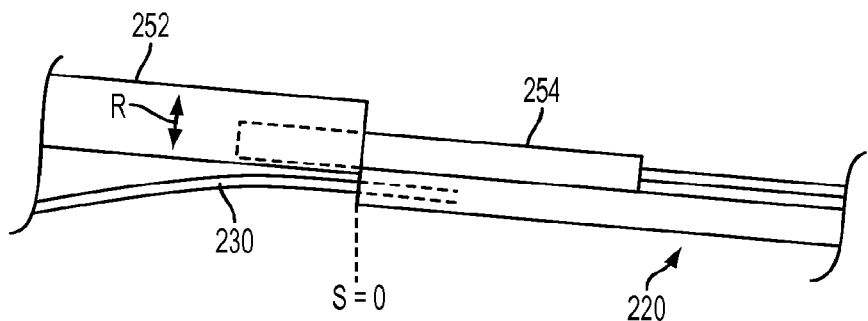
Figure 6D:
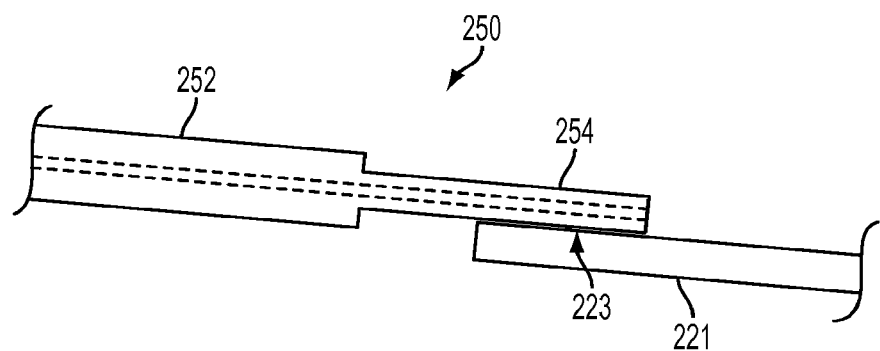
Figure 6E:
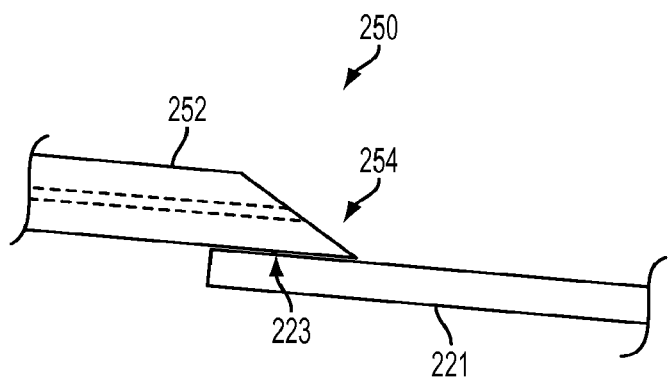
Figure 6F:
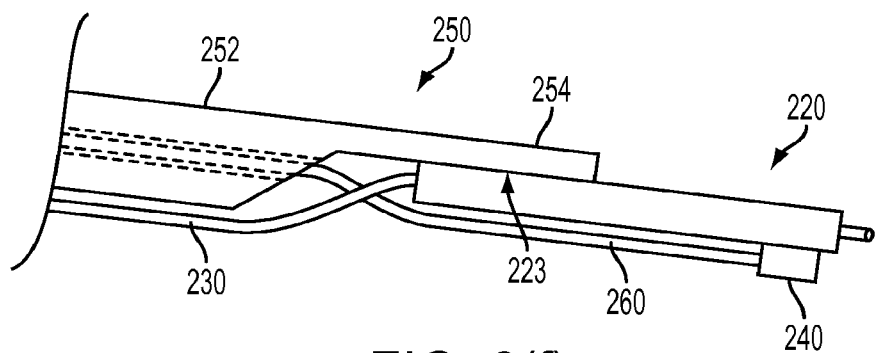
Figure 6G:
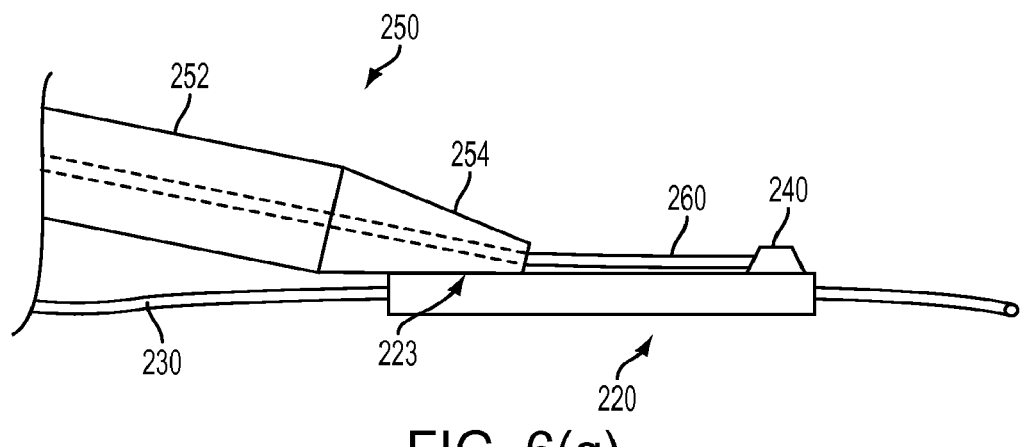

FIG. 6(a) shows an enlarged side view of a portion of the device 210 according to one embodiment of the invention. The delivery tube (proximal portion 250) and distal sleeve 220 are preferably coupled together using a flexible bond method (medical adhesive) to maintain flexibility of the device 210. In some preferred embodiments, for example, the proximal portion 250 will be bonded to an outer surface 221 of the distal sleeve 220 in a bonding area 223. Bonding area 223 is preferably disposed on distal sleeve 220 sufficiently proximal of the sensor 240 so that bonding area 223 is not within the vascular structure or passage of interest (e.g., it is not within the arterial vessel near a stenosis), but would still be inside the guiding catheter 232. The joining or bonding area 223 preferably maintains a degree of flexibility in order to accommodate bends such as that in the aortic arch. As previously noted, it may be desirable to minimize the width of the device 210 so that it can be passed through a relatively small guiding catheter 232, for example. This goal may be achieved, at least in part, by causing the bonding area 223 to be as narrow as possible. In some embodiments, it is desirable to use the sensor delivery device 210 inside a diagnostic guiding catheter 232, which are generally 4 Fr.

In some embodiments, the use of a distal transition 254 to couple the proximal portion 250 to the distal sleeve 220 may obtain a significant reduction in the width of the device 210. In certain preferred embodiments of the invention, the device 210 will be able to pass through a 4 Fr guiding catheter 232. The embodiment of FIG. 6(*a*) has a proximal portion 250 that comprises a main section 252 and a distal transition 254. Distal transition 254 extends distally from main section 252 and is coupled to an outer surface 221 of distal sleeve 220 at bonding area 223. As shown in FIG. 6(*a*), the use of a distal transition 254 to couple the proximal portion 250 to the distal sleeve 220 may cause a reduction in the width of the device 210 as compared to a device 210 without the distal transition 254. This may be accomplished, for example, in embodiments where the distal transition 254 is smaller in cross-sectional area than main section 252. (Of course, the distal transition 254 is optional and may not be required in all embodiments of the invention; the embodiments shown in FIGS. 1, 2, and 4, for example, do not include a distal transition. Such embodiments may result in a simpler manufacturing process, for example.)

In the embodiment shown in FIG. 6(*a*), distal transition 254 may be substantially coaxial and/or concentric with main section 252, and is smaller in diameter than main section 252. In some embodiments, distal transition 254 may be formed by inserting a hypotube inside the end of the proximal portion 250, the hypotube being of somewhat smaller diameter than the proximal portion 250. The hypotube distal transition 254 and the proximal portion may then be soldered together, as shown at 256. The distal sleeve 220, which may comprise a thin walled tube formed of a material such as polyimide, may then be bonded to the smaller diameter distal transition 254. Alternately, the distal sleeve 220 could be formed from a flat wire wound microcoil with PET tubing heat shrunk over the microcoil. An embodiment using a stainless steel microcoil for the distal sleeve 220 might provide a lower coefficient of friction (than polyimide, for example) to reduce the sliding friction. However, such a microcoil embodiment would probably benefit from the use of a PET tubing covering 226 to provide reinforcement and/or a smooth surface. PET tubing may be used to form covering 226, as shown in FIG. 6(*a*), and substantially as described above. Once the PET tubing covering 226 has been heat shrunk in the area of distal transition 254, for example, covering 226 may have one or more openings 227 formed in the PET tubing, for example, to create an exit port 227 for the guidewire 230, as shown. Note that, although only shown in FIG. 6(*a*), the embodiments shown in FIGS. 6(*a*), 6(*b*), and 6(*c*) may all include an optional covering 226 (e.g., PET tubing), according to certain embodiments of the invention.

FIG. 6(*b*) shows an embodiment of the invention in which the longitudinal axis of distal transition 254 is offset radially some distance "R" from the longitudinal axis of main section 252 to provide a further potential reduction in the width of device 210, for example, to minimize the footprint of device 210 and allow the use of a relatively small guiding catheter. FIG. 6(*c*) shows an embodiment where the radial offset "R" is in an opposite direction from the offset "R" shown in FIG. 6(*b*). This arrangement may provide more clearance for guidewire 230 as it exits distal sleeve 220 in the area near distal transition 254.

FIGS. 6(*a*) and 6(*b*) also illustrate techniques that may be employed to form the distal transition 254. For example, the distal transition 254 may be formed by welding or soldering a tubular member to the main section 252 as shown at 256. As shown, the tubular member 254 may extend into the end of main section 252, and may include a communication channel 260 (e.g., an extension of communication channel 260 within main section 252). Alternately, the distal transition 254 may be formed by "swaging" a distal end of the main section 252, as shown at 256. "Swaging," as that term is used herein, encompasses a number of manufacturing processes that reduce the diameter of a workpiece, for example, by forcing the workpiece (or a portion thereof) through a confining die, or by hammering a round workpiece into a smaller diameter workpiece (e.g., rotary swaging or radial forging, for example).

Other methods of forming the distal transition 254 may include grinding (e.g., to reduce the outer diameter of a single piece from that of main section 252 to that of distal transition 254), or the use of adhesives or glue (e.g., epoxy, ultraviolet adhesives, cyanoacrylates, etc.), or thermoforming, and/or other techniques known to those of ordinary skill in this area. FIGS. 6(*d*) and 6(*e*) show exemplary embodiments that may be formed by grinding or other comparable techniques, for example. Further, distal transition 254 need not extend into the main section 252 and could instead be held in an abutting relationship to main section 252 using certain of the aforementioned techniques.

FIGS. 6(*a*) and 6(*b*) happen to show embodiments of the invention in which a distal transition 254 is employed to "setback" the main section 252 from the distal sleeve 220 a distance "S" as shown. This may, for example, be advantageous in creating additional "clearance" for the guidewire 230 as it exits the distal sleeve 220. However, the setback is not a requirement, and embodiments of the invention may be employed with a zero setback, as shown in FIG. 6(*c*) (e.g., S=0).

Figure 7A:
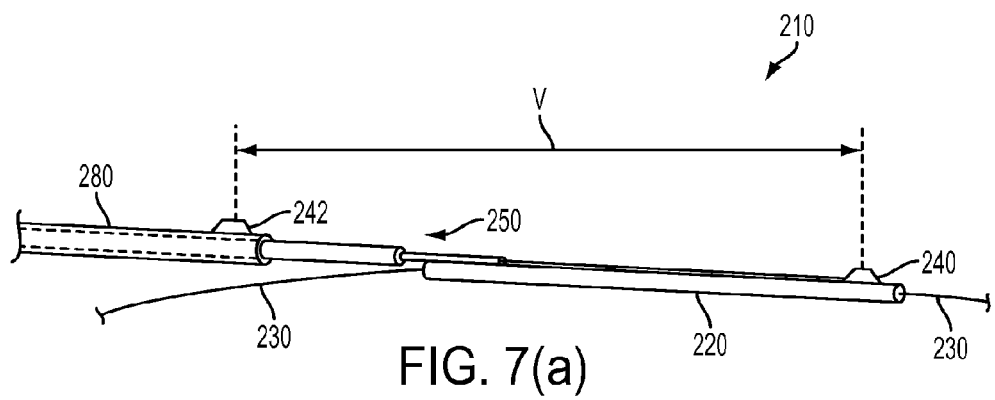
FIGS. 7(a) and 7(b) are perspective views of a sensor delivery device having a second sensor disposed on a proximal sleeve according to an embodiment of the invention.
Figure 7B:
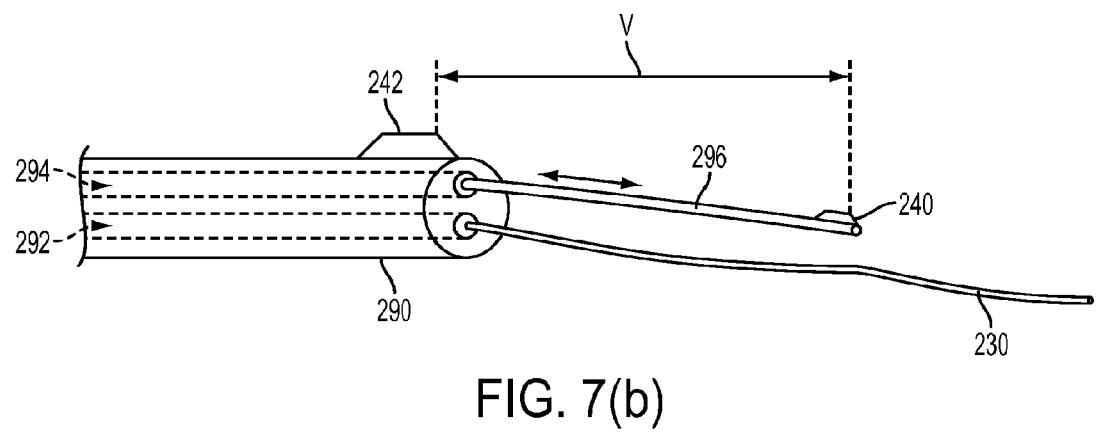

FIG. 7(*a*) shows one possible embodiment of the invention in which a second sensor 242 is coupled to a proximal sleeve 280, which thereby allows the first and second sensors 240, 242 to be spaced apart a variable distance, "V," as shown. Proximal sleeve 280 in such an embodiment is adapted to be moved longitudinally (e.g., advanced and/or refracted) by an operator by sliding over proximal portion 250 to achieve the desired spacing, "V," as shown.

FIG. 7(*b*) shows an alternate embodiment in which a multilumen shaft 290 (e.g., formed of a polymer) includes a guidewire lumen 292, a sensor lumen 294 for an extendible/retractable first sensor 240 disposed on a distal end of an extendible/retractable sensor shaft 296, the sensor shaft 296 being slidably received within sensor lumen 294, and a second sensor 242 coupled to an outer portion of the multilumen shaft 290. The first and second sensors 240, 242 may be spaced a variable distance apart (e.g., across a stenotic lesion of other anatomical location of interest in a patient) by slidably moving the sensor shaft 296 with respect to the multilumen shaft 290 (e.g., by moving sensor shaft 296 within sensor lumen 294).

Figure 8:
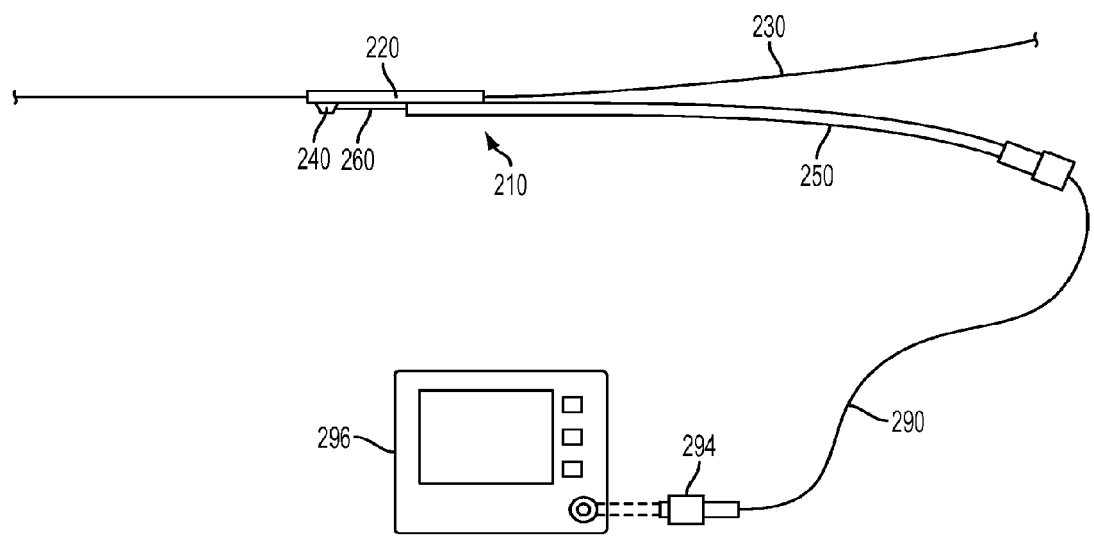
FIG. 8 is a perspective view of a sensor delivery device having a furcation tube according to an embodiment of the invention.

FIG. 8 shows a device 210 according to an embodiment of the invention in which a proximal end of proximal portion 250 interconnects with a fiber optic furcation tube 290 (e.g., in embodiments of the invention employing a fiber optic sensor). A fiber optic furcation tube 290 provides an extension of the fiber optic communication channel 260 (from the sensor 240 through the proximal portion 250), to an optional connector 294, such as an "SC" fiber optic connector. (An SC connector is a fiber optic connector with a push-pull latching mechanism which provides quick insertion and removal while also ensuring a positive connection. It also follows certain industry standards, allowing interconnection with a variety of fiber optic devices which follow the same standards.) Furcation tube 290 may, for example, be provided with SC connector 294 to allow the device 210 to send a signal from sensor 240, for example, to other devices, monitors, fluid injection devices, display and control units, etc. Furcation tube 290 may comprise a Kevlar fiber reinforced tube (e.g., for strength) according to some embodiments. In some alternate embodiments, furcation tube 290 could be formed of coaxial tubing.

The length of furcation tube 290 may be chosen to extend from the device 210 in the sterile field (e.g., where the patient is) to a location outside of the patient, such as a medical fluid injector, or to a standalone display device, or to some other processing or computing equipment 296 positioned some distance from the patient. The SC connector 294 is adapted to interconnect with an injector (or other signal processing unit) appropriately configured. If signal processing is done within the injector, then the injector display could be utilized to display pressure waveforms and/or to calculate and display FFR values.

Figure 9:
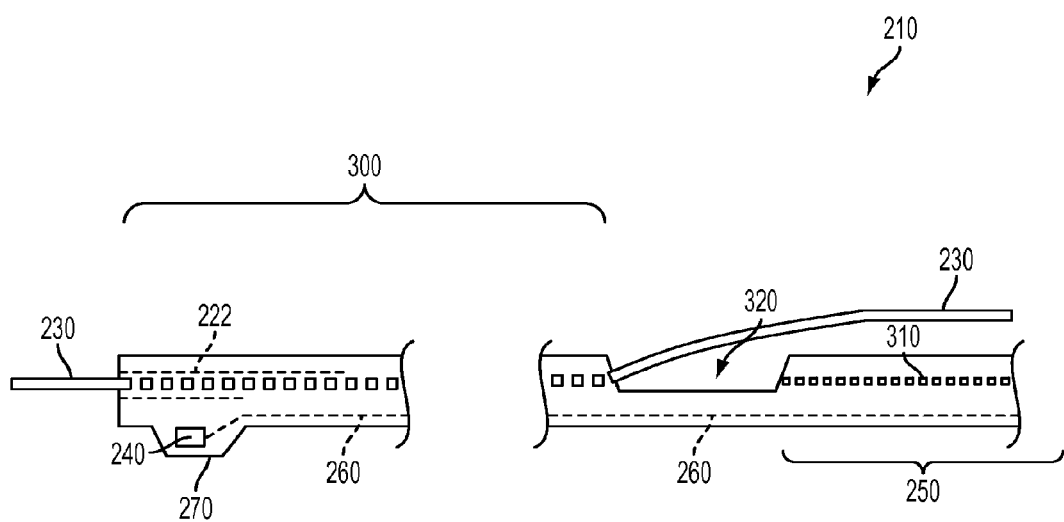
FIG. 9 is a cross-sectional side view of a sensor delivery device having a dual lumen configuration according to one embodiment of the invention.

An alternate embodiment of the invention would be to construct a distal portion 300 of the sensor delivery device 210 using a dual lumen configuration. An example of such an embodiment is illustrated in FIG. 9. One lumen of the distal portion 300 would accommodate the fiber optic communication channel 260 from the sensor 240 (and from sensor housing 270, in some embodiments). The other lumen (e.g., guidewire lumen 222) would be adapted to slide over the guidewire 230 as shown. The guidewire 230 in such an embodiment would exit from the dual lumen distal portion 300 a certain distance (e.g., about 10-12 inches) back from (e.g., proximal to) the sensor 240 through an opening 320 in the device 210. In some embodiments, a stiffening wire 310 could be placed in the remaining proximal portion of the lumen 222 (that is, the portion of the guidewire lumen 222 in the proximal portion 250 of device 210). The stiffness of the stiffening wire 310 could be varied, for example, to aid a physician in deploying and positioning the device 210 through a catheter and into a particular anatomical (e.g., vascular) structure of interest. The stiffening wire 310 could be part of the dual-lumen device 210, or could be an optional, removable item selected by a physician to obtain the desired amount of stiffness according to some embodiments.

Another alternate embodiment of the invention would be an entirely over-the-wire (OTW) device, substantially as shown in FIG. 10. FIG. 10 illustrates an embodiment of the invention in which both the distal sleeve 220 and the proximal portion 250 of sensor delivery device 210 are adapted to slide over a guidewire 230. The guidewire 230 in such an embodiment would not exit from or separate from the device 210 at some point along the length of device 210. Instead, the entire length of the proximal portion 250 of device 210 would slide over the guidewire 230 within a guiding catheter (not shown). The design of the device may incorporate two different sizes of tubes, for example, to form the distal sleeve 220 and proximal portion 250. For example, a smaller diameter thin-walled tube could form the distal sleeve 220, where the sensor 240 resides (optionally, within a sensor housing 270). Back some distance from the location of sensor 240 on the distal sleeve 220, the smaller diameter tube of the distal sleeve 220 would transition into a larger diameter portion (e.g., proximal portion 250), with sufficient clearance between the inner wall of both tubes and the guidewire. Such clearance may provide less friction and sliding resistance while positioning the sensor 240, for example. The larger diameter tube of the proximal portion 250 could be made, for example, from a material with a low coefficient of friction to lower the sliding force. The sensor 240 (and sensor housing 270, where applicable) could be of similar construction to that described above with respect to FIGS. 5(a)-5(d).

FIG. 10 is an example of an embodiment of the invention that illustrates the over-the-wire concept. The larger diameter tubing of the proximal portion 250 could be formed of a single lumen tube or a dual lumen tube. With a single lumen tube, the communication channel 260 (e.g., fiber optic) could be disposed on an outer surface of the proximal portion 250, for example, and could extend toward a connector at a proximal end of the device 210. In embodiments with a dual lumen tube forming the proximal portion 250, the communication channel 260 could extend toward a connector at a proximal end of the device 210 within the second lumen. This could, for example, provide added protection for the communication channel 260 (e.g., fiber optic).

Figure 11:
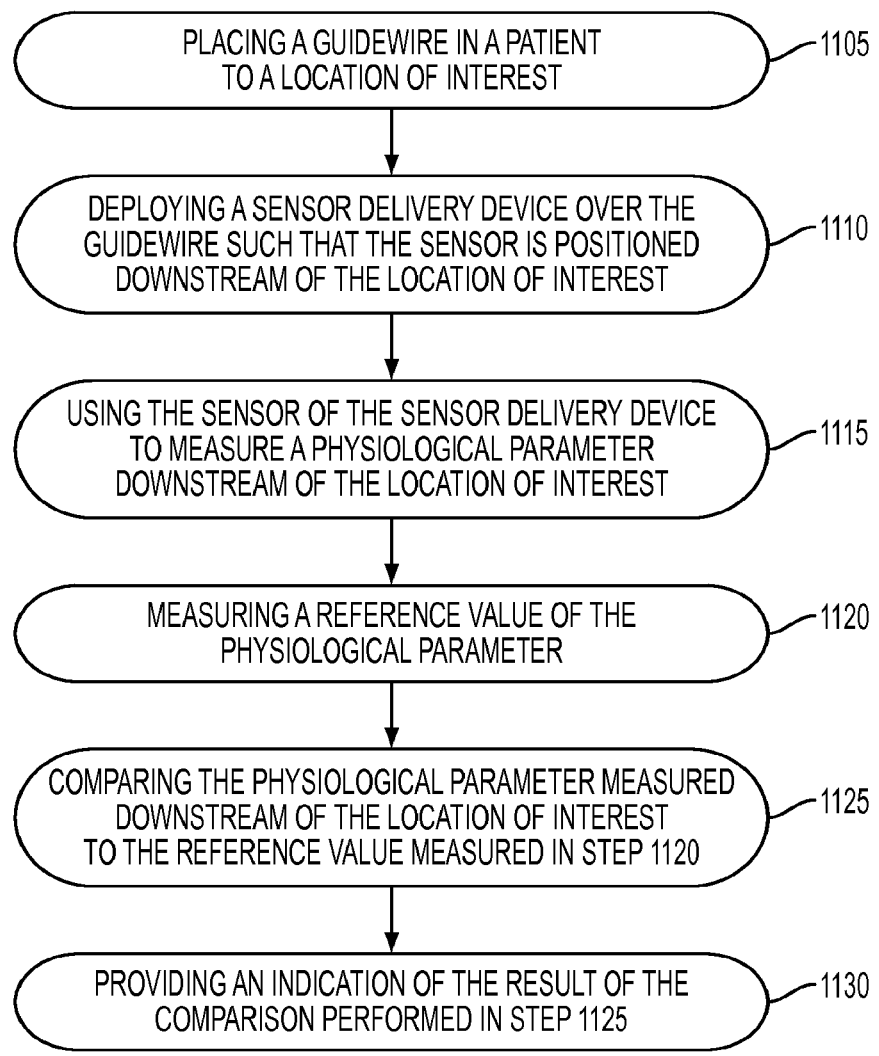
FIG. 11 is a flow diagram showing a method of using a sensor delivery device according to certain embodiments of the invention.

FIG. 11 is a flow diagram showing a method of using a sensor delivery device according to certain embodiments of the invention. In a preferred embodiment of the invention, for example, the method may be used to assess the severity of a stenotic lesion in a patient's vasculature. Step 1105 comprises placing a guidewire in a patient to a location of interest. In some embodiments, this may be a diagnostic guidewire, and a guiding catheter may also be inserted into the patient in conjunction with the guidewire. Step 1110 comprises deploying a sensor delivery device over the guidewire such that the sensor is positioned downstream of the location of interest (e.g., downstream of a stenotic lesion). In some embodiments, the sensor delivery device will have a sensor mounted to a distal sleeve that slides over the guidewire, and a proximal portion that is used to advance the distal sleeve over the guidewire without having to move the guidewire. Step 1115 comprises using the sensor of the sensor delivery device to measure a physiological parameter of interest at the location of interest. In some embodiments, the physiological parameter is blood pressure downstream of a stenotic lesion, $P_d$. Step 1120 comprises measuring a reference value of the physiological parameter of interest. In some embodiments, this step comprises measuring blood pressure upstream of a stenotic lesion, $P_p$. This could be done, for example, with a separate blood pressure monitoring apparatus, according to some embodiments, or could be done by repositioning the sensor delivery device to a location upstream of the stenotic lesion and making a second pressure measurement with the sensor of the device. Step 1125 may be an optional step which comprises comparing the physiological parameter of interest measured at the location of interest to the reference value measured in step 1120. In some embodiments, this may comprise calculating a ratio of the two measured values. In one preferred embodiment of the invention, step 1125 comprises calculating FFR as the ratio of downstream to upstream blood pressures, $P_d/P_p$. Step 1130 may be an optional step which comprises providing an indication of the result obtained in step 1125. For example, step 1130 may comprise providing a visual indication of the calculated FFR value, or may provide other visual cues (e.g., providing a color-coded indication of the severity of a stenotic lesion, such as a red indicator for FFR values less than 0.75, and a green indicator for FFR values equal to or greater than 0.75, as possible examples).

Figure 12:
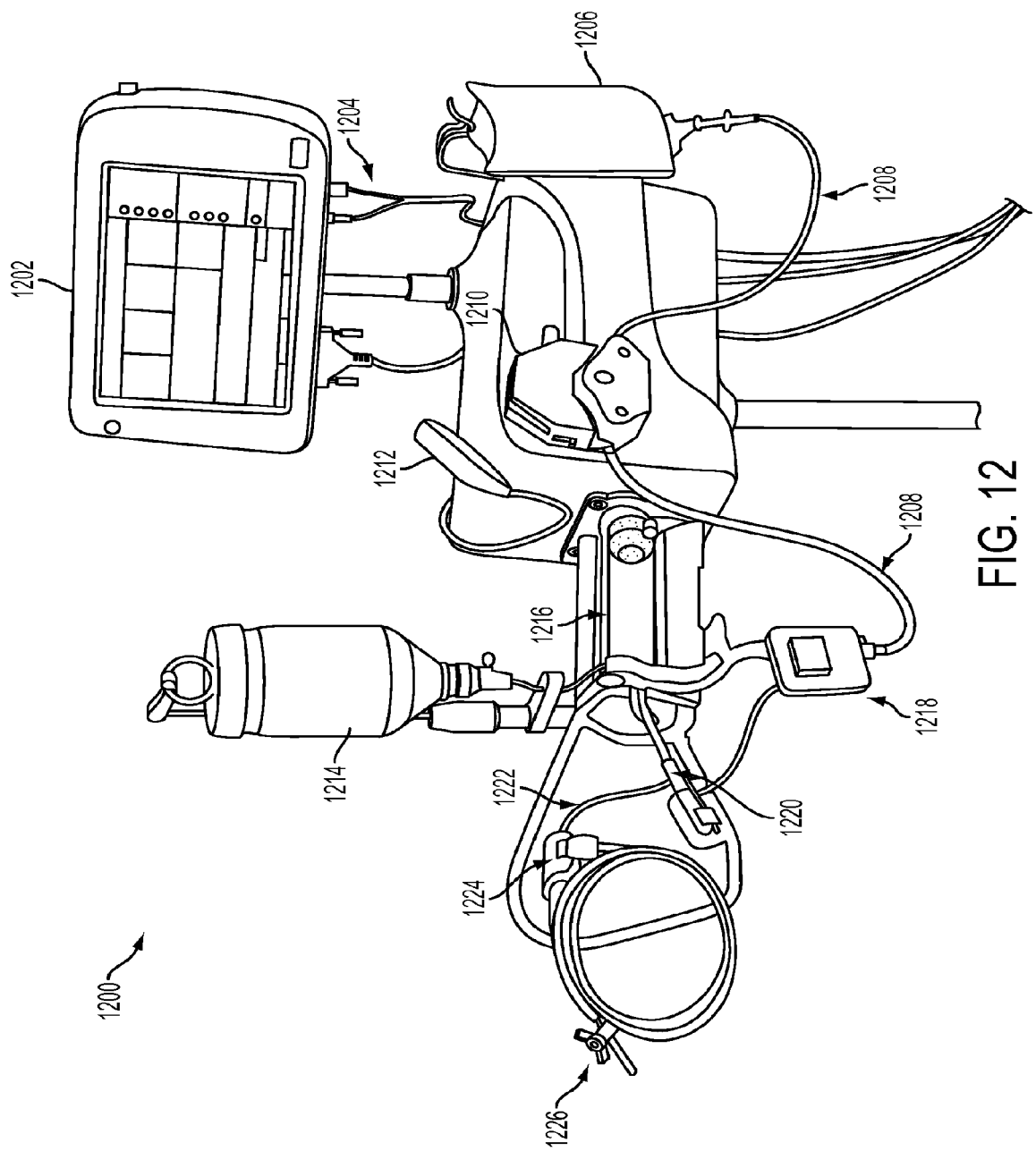
FIG. 12 is a perspective view of a fluid injection system that may be used to interact with a sensor delivery device according to an embodiment of the invention.
Figure 13:
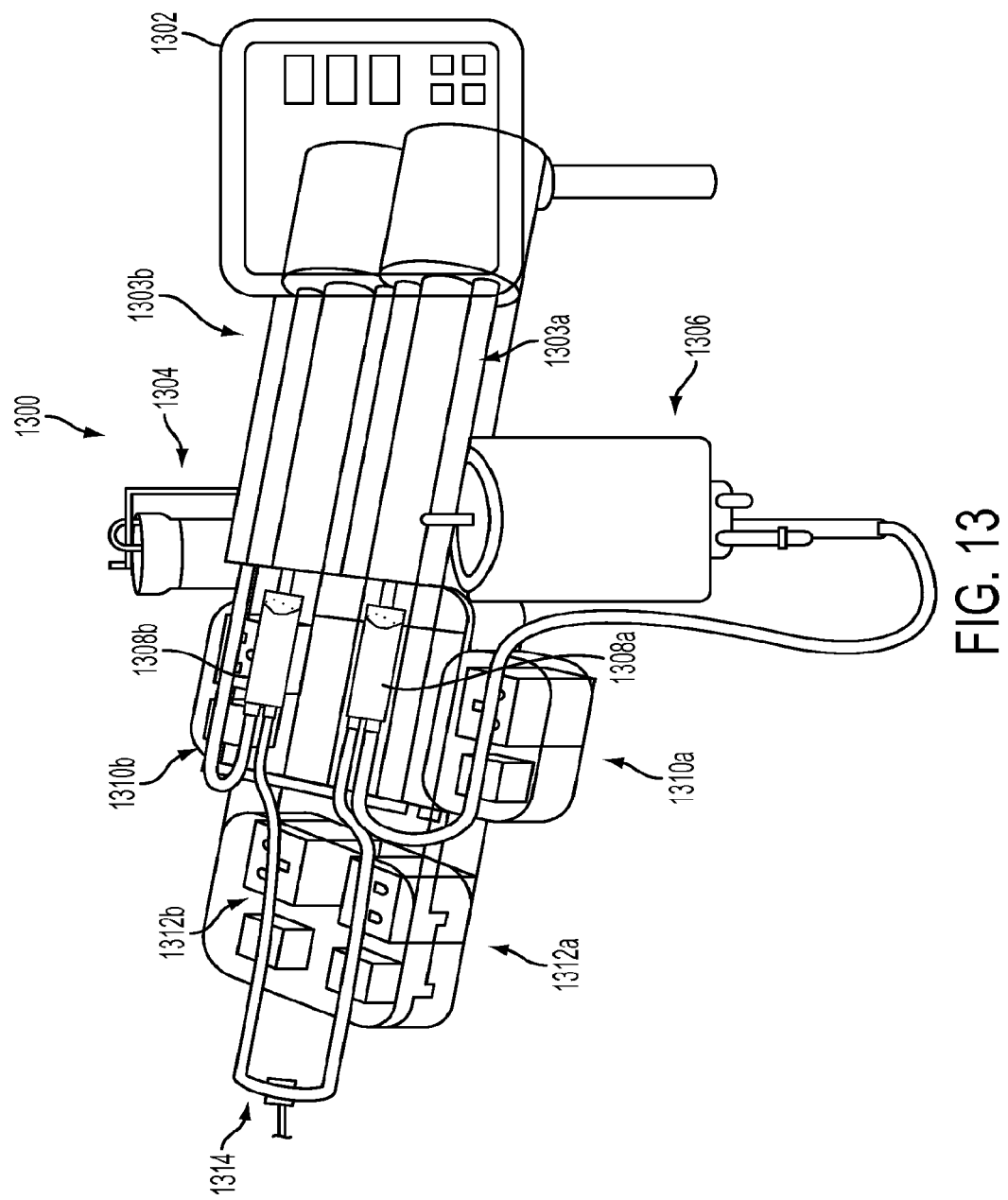
FIG. 13 is a perspective view of a fluid injection system that may be used to interact with a sensor delivery device according to an embodiment of the invention.

It may be desirable, as mentioned above with respect to FIG. 8, to have the sensor delivery device 210 interact with other devices and/or display equipment. For example, a furcation tube 290 and a connector 294 may be used to send the signal (e.g., the measured physiological parameter signal) from sensor 240 to processing device 296. Processing device 296 could be, for example, a standalone display monitor to show signal waveforms and/or numerical values of the physiological parameter signal from sensor 240. Processing device 296 could include data recording capabilities in some embodiments. In certain preferred embodiments of the invention, processing device 296 could comprise a medical fluid injection system, such as a powered fluid injector used to inject contrast media and/or saline during certain imaging procedures (e.g., angiography, computed tomography, MRI, ultrasound, etc.). FIGS. 12 and 13 illustrate exemplary powered injection systems which may be used with a sensor delivery device according to various embodiments of the invention.

FIG. 12 is a perspective view of one embodiment of a powered injection system 1200 that may be used to perform various functions and, when operable, may be coupled to a physiological sensor delivery device, such as the various embodiments of a sensor delivery device described above. The powered injection system 1200 shown in FIG. 12 may be used to inject medical fluid, such as contrast media or saline, into a patient within the sterile field during a medical procedure (such as during an angiographic or CT procedure). A physiological sensor delivery device may be coupled to the system 1200 and used within the sterile field during a patient procedure, according to one embodiment. The system 1200 includes various components, such as a control panel 1202, a hand-controller connection 1204, a hand controller 1212, a fluid reservoir 1206, tubing 1208, a pump 1210, a pressure transducer 1218, a fluid reservoir 1214, an injection syringe 1216, high pressure injection tubing 1222, a valve 1220, an air detector 1224, and a stopcock 1226. In one embodiment, described in more detail below, the fluid reservoir 1206 comprises a container such as, for example, a bag or bottle of diluent (such as saline), the fluid reservoir 1214 comprises a container such as, for example, a bag or bottle of contrast media, and the pump 1210 comprises a peristaltic pump. In other embodiments, the pump 1210 may comprise other forms of pumping devices, such as a syringe, a gear pump, or other form of displacement pump. In some embodiments, the injection syringe 1216 (along with its associated plunger), which is a pumping device, may be replaced with another form of pumping device that delivers high-pressure fluid injections to a patient. An individual pumping device is capable of operating or functioning in different, or multiple, operational modes. For example, a pumping device may be operable to pump fluid when actuated, or driven, to move in a first direction (e.g., forward), while it may also be operable to move in a second direction (e.g., an opposite direction, backward) to carry out certain functions.

The system 1200 of FIG. 12 also shows a hand controller 1212 and an air detector 1224. An operator may use the hand controller 1212 to manually control injection of saline and/or contrast media. The operator may push a first button (not shown) on the hand control 1212 to inject saline, and may push a second button (not shown) to inject contrast, for example. In one embodiment, the operator may push on the contrast button to deliver contrast at a variable flow rate. The harder the operator pushes on the button, the greater the flow rate of contrast media delivered to the patient. Other controllers, such as foot pedal controllers, may also be used. The air detector 1224 is able to detect potential air bubbles or columns within the high-pressure tubing 1222. In one embodiment, the air detector 1224 is an ultrasonic or acoustic-based detector. In other embodiments, the air detector 1224 may use infrared or other detection means (such as optical). If the air detector 1224 detects the presence of air in the high-pressure tubing 1222, it generates a signal that is used to warn the operator and/or halt an injection procedure.

An operator may use the control panel 1202 to view and/or select various parameters and/or protocols to be used during a given procedure. The control panel 1202 may be used to display information to an operator about the status of the equipment and/or the patient. The pump 1210 may be used to pump saline from the bag into the patient via the saline tubing 1208, the valve 1220, and the high-pressure tubing 1222. In one embodiment, the valve 1220 comprises a spring-based spool valve, as is known in the art. In one embodiment, the valve 1220 comprises an elastomeric-based valve.

In one embodiment, the syringe 1216 is used to draw contrast from the reservoir 1214 into the syringe 1216, and to inject contrast from the syringe 1216 into the patient via the valve 1220 and high-pressure tubing 1222. In one embodiment, the syringe 1216 is a self-purging syringe that has one port for filling of contrast and purging of air, and a second port for injection of contrast.

The valve 1220 may be used to control coupling between input ports to the valve 1220 and an output port. In one embodiment, the valve includes two input ports, one which is coupled to the contrast fluid line and another which is coupled to the saline fluid line. The saline fluid line also includes a pressure transducer 1218 for providing a signal representative of patient blood pressure, for example.

The stopcock 1226 regulates the flow of fluids to the patient. In one embodiment, the valve 1220 allows either the saline line or the contrast line to be coupled to the patient (high-pressure tubing) line 1222. When the syringe 1216 is used to inject contrast media, for example, the valve 1220 may allow the contrast media to flow to the patient line 1222 while blocking the flow of saline to the patient line 1222. Valve 1220 may operate such that the pressure transducer 1218 may also be blocked or isolated from the patient line 1222 during high-pressure injections, for example, to protect the transducer 1218 from high injection pressures that may accompany a contrast injection. When there is no injection of contrast from the syringe 1216, the valve 1220 may operate to block the contrast line from the patient line 1222, while opening the fluid connection between the saline line (tubing) 1208 and the patient line 1222. In this state, the pump 1210 is capable of injecting saline into the patient, and the pressure transducer 1218 is also capable of monitoring hemodynamic signals coming from the patient via the patient line 1222 and generating representative signals based upon the measured pressures.

As noted above, the system 1200 of FIG. 12 may be adapted to be coupled to a physiological sensor delivery device according to certain embodiments of the invention. System 1200 may, for example, be adapted to receive the physiological signal generated by the sensor 240 of device 210. In embodiments where the physiological signal from device 210 is a pressure signal measured downstream of a stenotic lesion (e.g., $P_d$), system 1200 may facilitate calculation of FFR, for example, since $P_p$ may already be provided by pressure transducer 1218 of system 1200. A visual or graphical display of the calculated FFR value could be presented to an operator via control panel 1202, for example. Since instantaneous values of $P_p$ and $P_d$ are available in such an arrangement, the timing effects and associated errors noted above with respect to FIG. 3 would not pose a problem—simultaneous measurement of $P_p$ and $P_d$ would reduce or eliminate such errors. In addition, time averaging or other signal processing could be employed by system 1200 to produce mathematical variants of the FFR calculation (e.g., mean, max, min, etc.). Alternately, a time-varying display or plot of the calculated FFR value could be displayed as a waveform (e.g., as a function of time).

FIG. 13 is a perspective view of another embodiment of a powered injection system 1300 that may be used to perform various functions and, when operable, may be coupled to a physiological sensor delivery device, such as the embodiments described above. The powered injection system 1300 shown in FIG. 13 may be used to inject medical fluid, such as contrast media or saline, into a patient within the sterile field during a medical procedure (such as during an angiographic or CT procedure). A physiological sensor delivery device may be coupled to the system 1300 and used within the sterile field during a patient procedure, according to one embodiment.

The system 1300 of FIG. 13 is a dual-syringe system that includes a control panel 1302 and two motor/actuator assemblies 1303a and 1303b. Each motor drives one of the linear actuators in the assemblies 1303a, 1303b. Each linear actuator drives a plunger of one syringe 1308a or 1308b. An individual plunger moves within the syringe barrel of the syringe 1308a or 1308b in either a forward or rearward direction. When moving in a forward direction, the plunger injects liquid into the patient line or purges air out of the syringe and into a liquid container (e.g., bottle). When moving in a rearward direction, the plunger fills liquid into the syringe 1308a, 1308b from a liquid container. FIG. 13 shows examples of two such liquid containers 1304 and 1306. In one embodiment, the container 1304 is a bag or bottle containing contrast agent, and the container 1306 is a bag or bottle containing diluent, such as saline. In other embodiments, the syringes 1308a, 13808b (along with associated plungers), which are each pumping devices, may either separately or together comprise another form of pumping device that is capable of injecting fluids at appropriate flow rates/pressures/etc., such as, for example, a peristaltic pump or another form of displacement pump. An individual pumping device is capable of operating or functioning in different, or multiple, operational modes. For example, a pumping device may be operable to pump fluid when actuated, or driven, to move in a first direction (e.g., forward), while it may also be operable to move in a second direction (e.g., an opposite direction, backward) to carry out certain functions. Multiple sets of pinch valve/air detect assemblies are shown both FIG. 13. One pinch valve/air detect assembly 1310a is coupled between the liquid container 1306 and a syringe input port of the syringe 1308a, and a second pinch valve/air detect assembly 1312a is coupled between a syringe output port of the syringe 1308a and the patient connection. A third pinch valve/air detect assembly 1310b is coupled between the liquid container 1304 and a syringe input port of the syringe 1308b, and a fourth pinch valve/air detect assembly 1312b is coupled between a syringe output port of the syringe 1308b and the patient connection. In the embodiment shown in FIG. 13, each syringe 1308a, 1308b is a dual-port syringe. Fluid flows and is drawn into the syringe 1308a or 1308b from a container via the syringe input port, and fluid flows out of and is injected from the syringe 1308a or 1308b via the syringe output port.

Each pinch valve is a pinch valve/air detect assembly 1310a, 1310b, 1312a, 1312b may be opened or closed by the system 1300 to control the fluid connections leading to or away from each of the syringes 1308a, 1308b. The air detect sensors in the assemblies 1310a, 1310b, 1312a, 1312b may be optical, acoustic, or other form of sensor. These sensors help detect air that may be present in the fluid connections leading to or away from the syringes 1308a, 1308b. When one or more of these sensors generates a signal indicating that air may be present in a fluid line, the system 1300 may warn the user or terminate an injection procedure. The use of multiple pinch valves within the system 1300 allows the system 1300 automatically, or through user interaction, selectively control the flow of fluid into or out of the syringes 1308a, 1308b by opening or closing fluid tubing. In one embodiment, the system 1300 controls each of the pinch valves. The use of multiple air-detect sensors helps improve the overall safety of the system 1300 by detecting possibly air (e.g., columns, bubbles) within fluid (in the tubing) leading to or away from the syringes 1308a, 1308b. Signals from the air detectors are sent to and processed by the system 1300, such that the system 1300 may, for example, provide a warning, or terminate an injection procedure, if air is detected. In the example of FIG. 13, the fluid tubing first flows through a pinch valve and then flows through an air detector within the assemblies 1310a, 1310b, 1312a, 1312b. In other embodiments, other configurations, ordering, and the like may be used for the pinch valves and air detectors within these assemblies. Moreover, other types of valves may be substituted for the pinch valves.

An operator may use the control panel 1302 to initialize, or setup, the injection system 1300 for one or more injection procedures, and may further use the control panel 1302 to configure one or more parameters (e.g., flow rate, volume of fluid to be delivered, pressure limit, rise time) of an individual injection procedure. The operator may also use the panel 1302 to pause, resume, or end an injection procedure and begin a new procedure. The control panel also displays various injection-related information to the operator, such as flow rate, volume, pressure, rise time, procedure type, fluid information, and patient information. In one embodiment, the control panel 1302 may be connected to a patient table, while being electrically coupled to the main injector of the system 1300. In this embodiment, the operator may manually move the control panel 1302 to a desirable location, while still having access to all functionality provided by the panel 1302.

The system of FIG. 13 also includes a valve 1314 coupled to both output lines coming from the syringes 1308a and 1308b. Each syringe output provides fluid injected through tubing that passes through a pinch valve/air detect assembly 1312a or 1312b and that then leads to an input of the valve 1314. In one embodiment, one fluid line to the valve 1314 also includes a pressure transducer. The valve output port of the valve 1314 is coupled to high-pressure tubing line, which is used to direct fluid to the patient. In one embodiment, the valve 1314 is made of a flexible material, such as an elastomeric material. The valve 1314 allows one of the fluid lines (e.g., the contrast line or the saline line) to be coupled to the patient (high-pressure tubing) line. When saline and contrast are contained within the syringes 1308a and 1308b, respectively, the valve 1314 allows the contrast media to flow from the syringe 1308b to the patient line (assuming the pinch valve in the assembly 1312b is open and there has been no air detected), but blocks the flow of saline from the syringe 1308a to the patient line. The pressure transducer coupled to the saline line (according to one embodiment) is also blocked from the patient line, thereby protecting the transducer from high injection pressures that may accompany a contrast injection. When there is no injection of contrast from the syringe 1308b, the valve 1314 blocks the contrast line from the patient line, but allows a connection between the saline line from the syringe 1306 to the patient line. The syringe 1308a is capable of injecting saline into the patient (assuming the pinch valve in the assembly 1312a is open and there has been no air detected), and the pressure transducer is also capable of monitoring hemodynamic signals coming from the patient via the patient line, and generating representative electronic signals based upon the measured pressures that can be processed by the system 1300.

In one embodiment, a secondary control panel (not shown) provides a subset of functions provided by the main panel 1302. This secondary control panel (also referred to herein as the "small" control panel) may be coupled to the injector within the system 1300. In one scenario, the operator may use the small panel to manage injector setup. The small panel may display guided setup instructions that aid in this process. The small panel may also display certain error and troubleshooting information to assist the operator. For example, the small panel may warn the operator of low contrast or saline fluid levels in the liquid reservoirs and/or syringes.

As with the system 1200 of FIG. 12, system 1300 of FIG. 13 may be adapted to be coupled to a physiological sensor delivery device according to certain embodiments of the invention. System 1300 may, for example, be adapted to receive the physiological signal generated by the sensor 240 of device 210. Processing of the physiological signal from sensor 240 (and/or from additional sensors of the sensor delivery device 210, if applicable) may be performed within the injection system 1200 or 1300, for example. Signal conditioning and/or processing may, for example, be performed by a circuit board or card that may be an add-on feature to system 1200 or 1300. Such a signal conditioning board or card may process a "raw" signal from sensor 240 and convert the signal into a standard analog and/or digital signal, which can be used by processors of the injector system, according to some embodiments. The processed signal may enable injector system 1200 or 1300 to display the signal data (e.g., as pressure waveforms), and/or perform algorithms and/or calculations and display the results.

In embodiments where the physiological signal from device 210 is a pressure signal measured downstream of a stenotic lesion (e.g., $P_d$), system 1300 may facilitate calculation of FFR, for example, since $P_p$ is already provided by the pressure transducer of system 1300. A visual or graphical display of the calculated FFR value, for example, could be presented to an operator via control panel 1302, for example, or via a small control panel (not shown) having a subset of the functions provided by control panel 1302. Since instantaneous values of $P_p$ and $P_d$ are available in such an arrangement, the timing effects noted above with respect to FIG. 3 would not pose a problem. In addition, time averaging or other signal processing could be employed by system 1300 to produce mathematical variants of the FFR calculation (e.g., mean, max, min, etc.).

Figure 14:
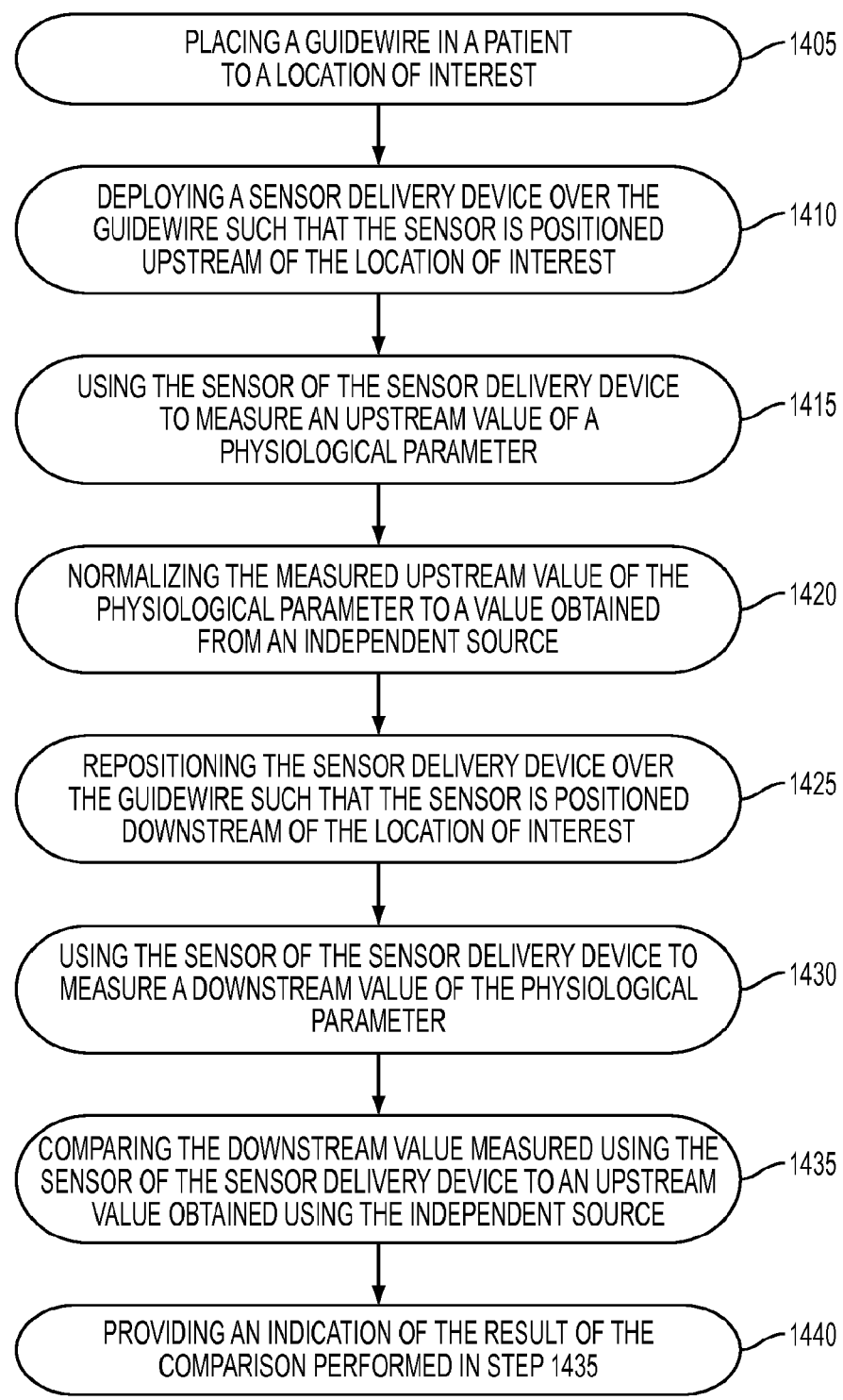
FIG. 14 is a flow diagram of a method of using a sensor delivery device in conjunction with a fluid injection system according to certain embodiments of the invention.

FIG. 14 is a flow diagram of a method that may be performed according to one embodiment of the invention. The methods described herein may be performed in varying degrees of automation, for example, by having instructions stored in a computer-readable medium and/or performed by a computer or processor associated with a powered injection system (such as the ones described above with respect to FIGS. 12 and 13, or other comparable fluid injection systems). The method of FIG. 14 may, for example, be used to assess the severity of a fluid flow restriction in a patient according to some embodiments of the invention. This method may be performed using various powered injection systems, such as the system 1200 shown in FIG. 12, or the system 1300 shown in FIG. 13. The ordering of the actions shown in FIG. 14 is for exemplary purposes only. In one embodiment, a powered injection system may be capable of performing some of the steps of the method shown in FIG. 14 automatically, or alternately, after the operator has requested that the method be commenced through manual activation on the control panel (or secondary panel, if available).

Step 1405 in FIG. 14 comprises placing a guidewire in a patient to a location of interest, such as a stenotic lesion, or across a heart valve, for example. In some embodiments, this may be a diagnostic guidewire, and a guiding catheter may also be inserted into the patient in conjunction with the guidewire. Step 1410 comprises deploying a sensor delivery device over the guidewire such that the sensor is positioned upstream of the location of interest (e.g., upstream of a stenotic lesion, or on the high pressure side of a valve). In some embodiments, the sensor delivery device will have a sensor mounted to a distal sleeve that slides over the guidewire, and a proximal portion that is used by an operator to advance the distal sleeve over the guidewire to the desired location without having to move the guidewire. Step 1415 comprises using the sensor of the sensor delivery device to measure a value of the physiological parameter upstream of the location of interest. In some embodiments, the physiological parameter is blood pressure, and the pressure measured by the sensor upstream of a stenotic lesion is the proximal pressure, $P_p$.

Step 1420 in FIG. 14 comprises "normalizing" the $P_p$ measurement made in step 1415 to the $P_p$ measurement obtained from an independent source. "Normalizing" the $P_p$ measurement refers to the fact that an independent source (e.g., a fluid sensor for monitoring patient blood pressure during a procedure) will be used to obtain the $P_p$ value that will be used for later comparisons or calculations with the $P_d$ value (e.g., the downstream pressure) measured with the sensor of the sensor delivery device. The normalizing step basically ensures that the $P_p$ value measured with the sensor equals the $P_p$ value measured using the independent source so that no error is introduced (or that any error is minimized) when a subsequent downstream pressure measurement (e.g., $P_d$) is made. An adjustment, if needed, could be made to either $P_p$ value, although it may often be simpler to adjust the sensor-based $P_p$ value to match the independent source's $P_p$ value.

Step 1425 comprises deploying the sensor delivery device over the guidewire such that the sensor is downstream of the location of interest (e.g., downstream of the stenotic lesion). Step 1430 comprises using the sensor of the sensor delivery device to measure a downstream value of the physiological parameter. In some embodiments, this step comprises measuring blood pressure downstream of the stenotic lesion, $P_d$. Step 1435 comprises comparing the measured value downstream of the location of interest (e.g., $P_d$, downstream blood pressure) to a value measured upstream of the location of interest using the independent source (e.g., $P_p$). In some embodiments, the comparison made in step 1435 may comprise calculating a ratio of the two measured values. In one preferred embodiment of the invention, step 1435 comprises calculating FFR as the ratio of downstream to upstream blood pressures, $P_d/P_p$. Step 1440, which may be an optional step, comprises providing an indication of the result of the comparison made in step 1435. For example, step 1440 may comprise providing an indication of the calculated FFR value (e.g., numerical or graphical display or plot), and/or other cues may be provided to an operator. A color-coded indication of the severity of a stenotic lesion may be provided, for example, a RED indicator for FFR values less than 0.75, and/or a GREEN indicator for FFR values equal to or greater than 0.75. Other examples of indicators are possible, including non-visual indicators—an audible indication, an alarm sound for example, could alert an operator of an FFR value that is less than 0.75, which may prompt the operator to make a therapy decision.

Figure 15:
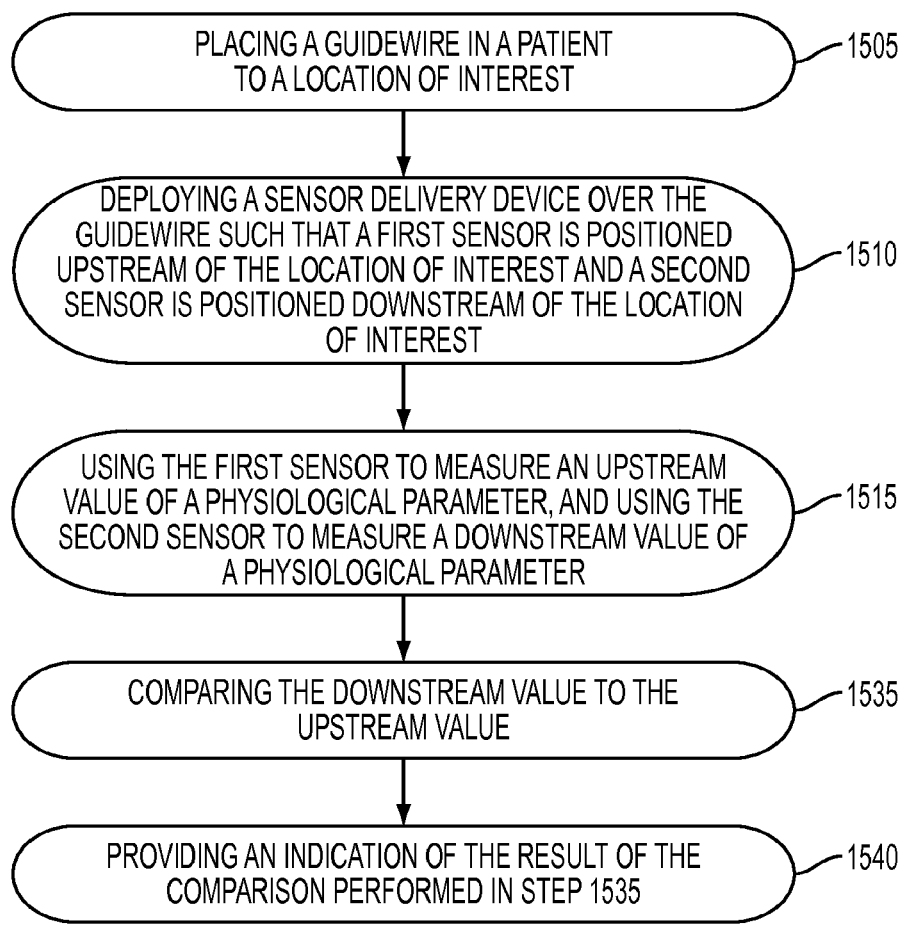
FIG. 15 is a flow diagram of a method of using a sensor delivery device according to an embodiment of the invention.

FIG. 15 is a flow diagram of a method that may be performed according to an embodiment of the invention. The method of FIG. 15 may, for example, be used to assess the severity of a fluid flow restriction in a patient according to some embodiments of the invention. The method of FIG. 15 employs a sensor delivery device 210 having a first and second sensor 240, 242, such as the devices 210 shown in FIGS. 2 and 7. This method may also be performed in conjunction with various powered injection systems, such as the system 1200 shown in FIG. 12, or the system 1300 shown in FIG. 13. The ordering of the actions shown in FIG. 15 is for exemplary purposes only.

Step 1505 in FIG. 15 comprises placing a guidewire in a patient to a location of interest, such as a stenotic lesion, or across a heart valve, for example. In some embodiments, the guidewire may be a diagnostic guidewire, and a guiding catheter may also be inserted into the patient in conjunction with the guidewire. Step 1510 comprises deploying a sensor delivery device over the guidewire such that a first sensor of the sensor delivery device is positioned upstream of the location of interest, and a second sensor of the sensor delivery device is positioned downstream of the location of interest. In an embodiment such as that described above with respect to FIG. 7, an optional step may next be performed wherein a proximal sleeve 280 is moved by an operator relative to the rest of device 210 in order to vary the distance, V, between first sensor 240 and second sensor 242. In an embodiment such as that described above with respect to FIG. 2, it should be noted that more than two sensors could be mounted along device 210, and that the spacing between adjacent sensors could vary as well, according to some embodiments of the invention. Step 1515 comprises using the first sensor to measure an upstream value of the physiological parameter, and using the second sensor to measure a downstream value of the physiological parameter.

Step 1535 comprises comparing the measured value downstream of the location of interest (e.g., $P_d$, downstream blood pressure) to the value measured upstream of the location of interest (e.g., $P_p$). In some embodiments, the comparison made in step 1535 may comprise calculating a ratio of the two measured values. In one preferred embodiment of the invention, step 1535 comprises calculating FFR as the ratio of downstream to upstream blood pressures, $P_d/P_p$. Step 1540, which may be an optional step, comprises providing an indication of the result of the comparison made in step 1535. For example, step 1540 may comprise providing an indication of the calculated FFR value (e.g., numerical or graphical display or plot), and/or other cues may be provided to an operator. A color-coded indication of the severity of a stenotic lesion may be provided, for example, a RED indicator for FFR values less than 0.75, and/or a GREEN indicator for FFR values equal to or greater than 0.75. Other examples of indicators are possible, including non-visual indicators—an audible indication, an alarm sound for example, could alert an operator of an FFR value that is less than 0.75, which may prompt the operator to make a therapy decision.

Although not shown in FIGS. 11, 14, and 15, any of these methods could be performed with an embodiment of device 210 having flow holes 224, such as the device of FIGS. 4(a) and 4(b). Using such a device, the methods may optionally include a step wherein an operator retracts the guidewire 230 to allow fluid flow (e.g., blood flow) through flow holes 224 into the guidewire lumen 222 of the distal sleeve 220. Performing this optional step prior to measuring downstream pressure, $P_d$, may reduce the amount of flow restriction caused by the device 210 itself, and may thereby reduce the measurement error.

In some embodiments, a method may include basing a therapy decision on the calculated FFR value, e.g., if the calculated FFR is less than 0.75, an interventional therapy is recommended and/or performed. In some embodiments, an interventional therapy device may be deployed by withdrawing sensor delivery device 210, and using the same guidewire 230 to deploy the interventional therapy device.

Figure 16:
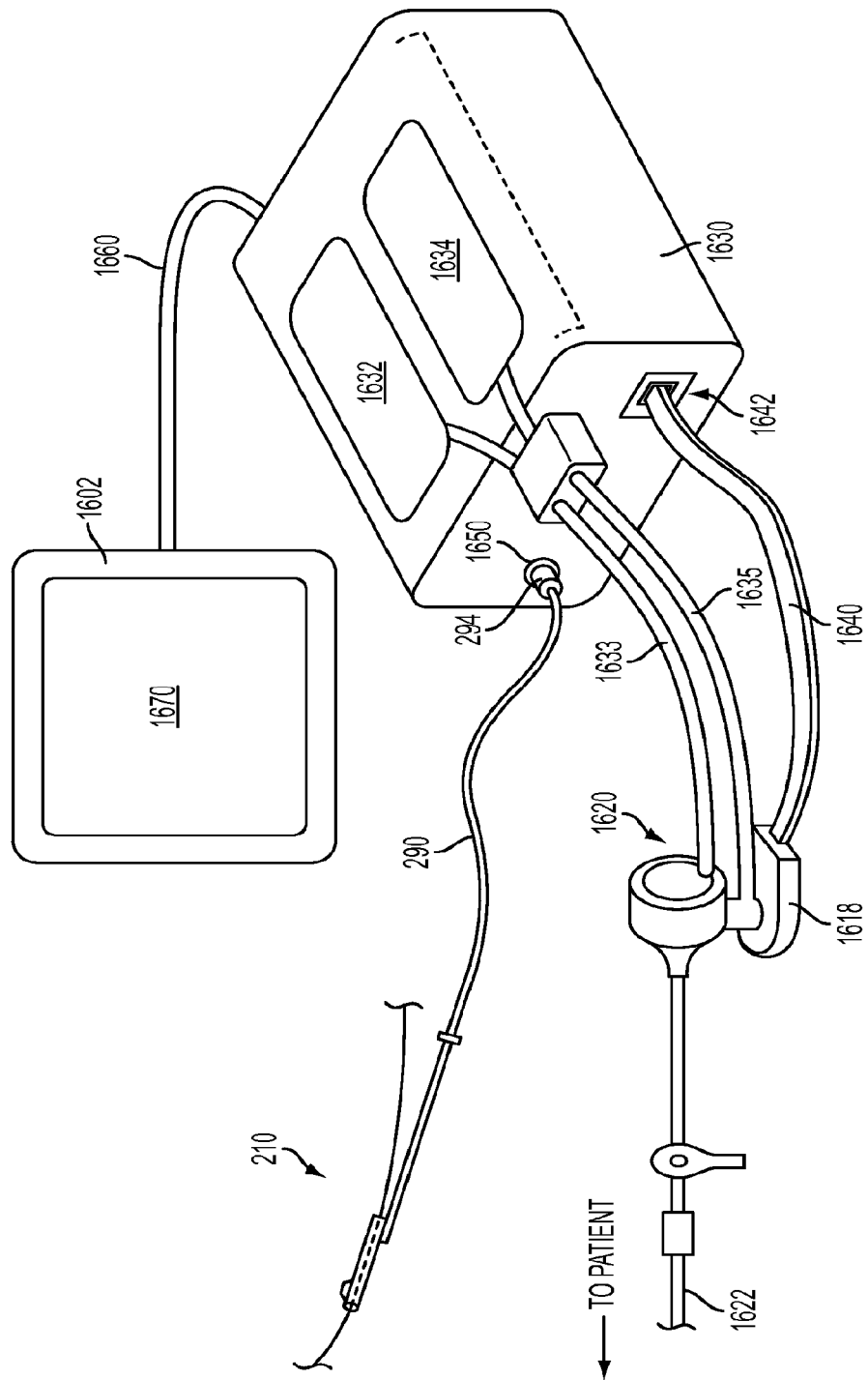
FIG. 16 is a perspective view of a powered injection system adapted to be coupled to a physiological sensor delivery device according to certain embodiments of the invention.

FIG. 16 is a perspective view of a powered injection system adapted to be coupled to a physiological sensor delivery device according to certain embodiments of the invention. FIG. 16 shows a sensor delivery device 210 connected to a powered injection system 1630 via furcation tube 290 and connector 294. Injection system 1630 is adapted to receive a physiological measurement signal (e.g., blood pressure) from device 210 via input port 1650. In preferred embodiments, the signal is an optical signal, and connector 294 is an SC fiber optic connector adapted to mate with port 1650 to receive the optical signal.

As shown in FIG. 16, system 1630 has 2 fluid containers 1632, 1634, which are adapted to deliver fluid through lines 1633 and 1635. Fluid in line 1633 (e.g., contrast solution) may be delivered at significantly higher pressures than fluid in line 1635 (e.g., saline solution), for example. Valve 1620 may be used to control coupling between input ports to the valve 1620 and to an output port which ultimately leads to a patient via patient line 1622. In one embodiment, valve 1620 includes two input ports, one which is coupled to a contrast fluid line 1633 and another which is coupled to a saline fluid line 1635. The saline fluid line is also coupled to a pressure transducer 1618 for providing a signal representative of patient blood pressure, for example. The signal from pressure transducer 1618 may be communicated to system 1630 via communication path 1640 and connector 1642, or via other equivalent means (e.g., infrared, optical, etc.).

In one embodiment, the valve 1620 allows either the saline line or the contrast line to be coupled to the patient (high-pressure tubing) line 1622. When the system 1630 is injecting contrast media, for example, the valve 1620 may allow the contrast media to flow to the patient line 1622 while blocking the flow of saline to the patient line 1622. Valve 1620 may operate such that the pressure transducer 1618 may also be blocked or isolated from the patient line 1622 during high-pressure injections, for example, to protect the transducer 1618 from high injection pressures that may accompany a contrast injection. When there is no injection of contrast from the system 1630, the valve 1620 may operate to block the contrast line from the patient line 1622, while opening the fluid connection between the saline line (tubing) 1635 and the patient line 1622. In this state, the system 1630 may be capable of injecting saline into the patient, while the pressure transducer 1618 is capable of monitoring hemodynamic signals coming from the patient via the patient line 1622, and generating representative signals based upon the measured pressures.

FIG. 16 shows control panel 1602 connected to injection system 1630 via communication path 1660. An operator may interact with system 1630 via control panel 1602 (or via a secondary panel, if available) to review and/or modify injection parameters, for example. In a preferred embodiment of the invention, system 1630 is adapted to receive pressure signals simultaneously from pressure transducer 1618 and from device 210, representative of downstream and upstream pressures (e.g., $P_d$, $P_p$), respectively. Thus, in a preferred embodiment, system 1630 receives $P_d$ and $P_p$ signals substantially simultaneously, compares the two signals (e.g., calculates FFR=$P_d/P_p$), and provides an indication of the result of the comparison to an operator via a display screen 1670 of control panel 1602. As noted above, the indication of the result of the comparison may take a number of different forms, including numerical, graphical, time plots, etc. The indication may be of the pass/fail variety, for example, indicating one color-coded pattern (e.g., a RED icon) for an FFR value below a certain value (e.g., 0.75), and/or a different color-coded pattern (e.g., a GREEN icon) for an FFR value at or above a certain value (e.g., 0.75). The indication may also be an audible alarm according to some embodiments of the invention.

Figure 17:
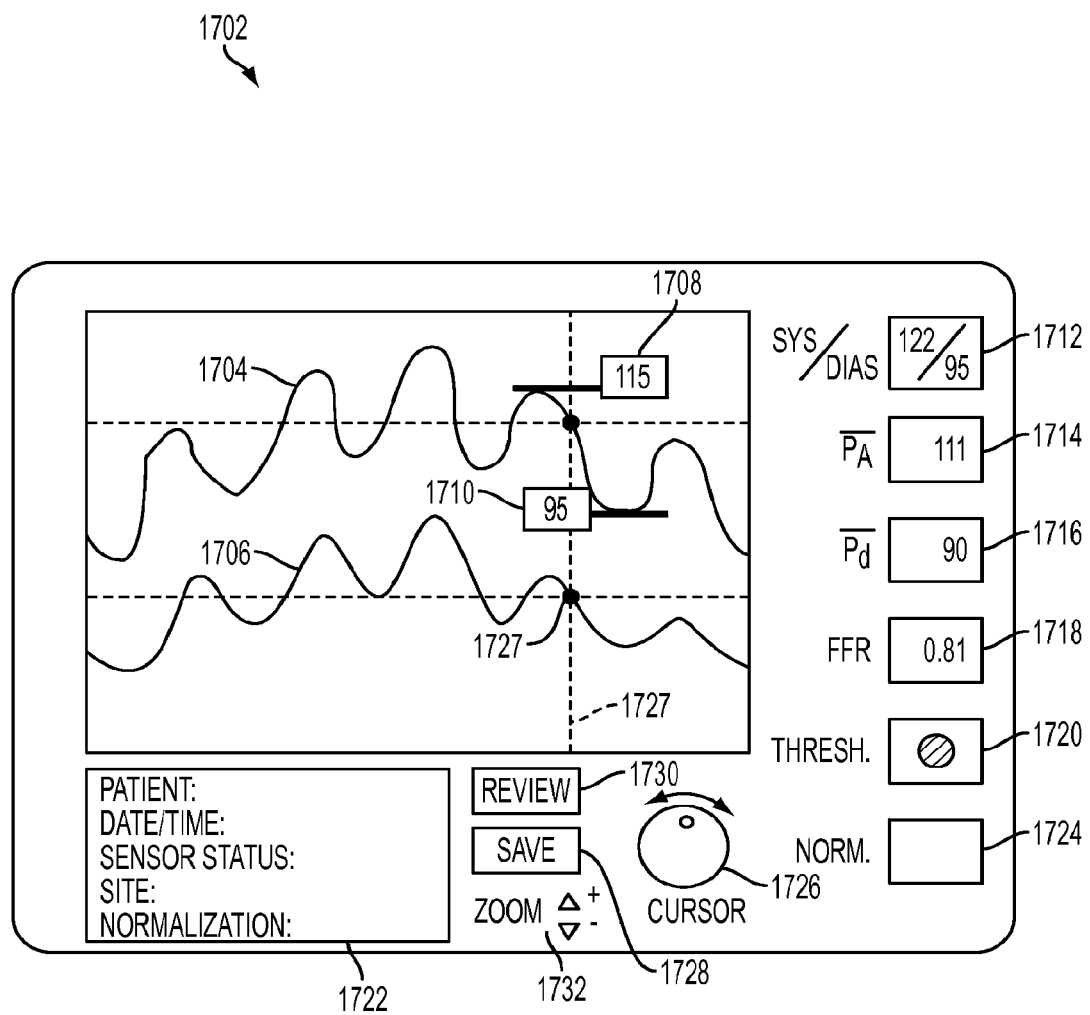
FIG. 17 is an idealized view of a user interface screen containing information that may be displayed to an operator, according to certain embodiments of the invention

FIG. 17 is an idealized view of information that may be displayed (e.g., via an interactive graphical user interface, or "GUI interface") to an operator, according to certain embodiments of the invention. FIG. 17 shows a GUI screen that may be displayed either via a control panel that is unique to the sensor delivery device 210, or via a control panel of a device adapted for use with device 210, such as the powered fluid injection systems described above with respect to FIGS. 12, 13, and 16. (The GUI interface could be implemented in software such that a user might see a very similar screen regardless of whether a stand-alone display device or an integrated injector system was being used, according to various embodiments of the invention.)

In FIG. 17, screen 1702 is adapted to display data in various forms (e.g., waveform data, numerical data, calculated values, patient information, device status information, etc.). For example, in a preferred embodiment of the invention useful for making FFR measurements, blood pressure waveforms may be displayed as a function of time for both proximal pressure, $P_p(t)$ 1704, and distal pressure, $P_d(t)$ 1706. In some embodiments, systolic and diastolic blood pressure measurements may be superimposed on the time plot for the proximal (e.g., aortic) pressure waveform, as shown at 1708 and 1710, respectively, and/or may be calculated as average values and displayed substantially as shown at 1712. Similarly, average values for proximal pressure 1704 and distal pressure 1706 may be calculated (e.g., these could be time-weighted averages, moving averages, etc.) and displayed as shown at 1714 and 1716, respectively. A calculation of FFR based on proximal pressure 1704 and distal pressure 1706 may also be calculated and displayed as shown at 1718, for example (e.g., FFR equals $P_p/P_d$, and the values used for $P_p$ and $P_d$ could be averages or other forms of statistical or numerical representation), according to some embodiments of the invention. Further, some embodiments may include a feature to alert an operator to an FFR value that lies outside of a normal range (e.g., less than 0.75) to indicate, for example, that some other action should be taken (e.g., select and perform an interventional therapy). This could be a visual cue (such as a colored light, as shown at 1720), or could be an audible cue (such as an alarm sound, for example).

The screen 1702 of FIG. 17 shows various additional features which may be (optionally or alternately) incorporated in various embodiments. Status area 1722, for example, may provide information about the patient, date/time, the site within a particular patient, the status of the sensor, and an indication of whether the sensor signal has been "normalized" to another pressure monitoring signal. A normalization button 1724 may be included in some embodiments, and could be used, for example, to normalize the pressure signal from a sensor of sensor delivery device 210. Normalization might be done during a procedure in which an FFR measurement is desired (e.g., to assess the severity of a stenosis). When a sensor of sensor delivery device 210 is positioned upstream of the stenosis, the measured pressure using the sensor should be equal to the proximal pressure measured using normal blood pressure monitoring equipment (e.g., via the pressure transducer 1618 of the injection system shown in FIG. 16, for example). In one embodiment, an operator would position the sensor 240 of sensor delivery device 210 upstream of a location of interest and press the normalization button 1724 of screen 1702, which could then automatically adjust or calibrate the pressure signal from sensor 240 to match the proximal pressure measured using normal blood pressure monitoring equipment.

The screen 1702 of FIG. 17 may also include navigational features, in some embodiments, which may allow an operator to view and record information that may be of interest. For example, a cursor button 1726 may allow an operator to position a marker or cursor 1727 to a point of interest on the waveforms 1704, 1706, which could provide instantaneous measured values of $P_p(t)$ 1704 and $P_d(t)$ 1706 at a selected point in time. In some embodiments, an operator may elect to save the cursored data by pressing a "save" button 1728, which could save the highlighted data for review at a later point in time. A review button 1730 may be provided for this purpose in some embodiments, allowing a user to compare previous historical measurements to current ones and use this information to make diagnostic and therapeutic decisions. In some embodiments, it may be desirable to include a "zoom" feature, for example, to analyze the data. For example, an operator may wish to zoom in (e.g., via the +arrow of zoom 1732) to look more closely at certain data, or may instead wish to zoom out (e.g., via the—arrow of zoom 1732) to evaluate overall trends, for example.

A Physiological Sensor Delivery Device has been described in connection with exemplary embodiments and exemplary preferred embodiments and implementations, as examples only. It will be understood by those having ordinary skill in the pertinent art that modifications to any of the embodiments or preferred embodiments may be easily made without materially departing from the scope of the appended claims.

What is claimed is:

1. A method of determining Fractional Flow Reserve (FFR) in a patient, the method comprising:

measuring, with a hemodynamic transducer or a sensor coupled to an intravascular sensor delivery device, a first blood pressure upstream of a location of interest in the patient during a phase of a cardiac cycle, measuring, with the sensor, a second blood pressure downstream of the location of interest in the patient in substantially the same phase of the cardiac cycle in which the first blood pressure was measured, and calculating, with a processor, FFR as a ratio of the first blood pressure to the second blood pressure, wherein the intravascular sensor delivery device comprises a distal sleeve and a proximal portion, the distal sleeve having a guidewire lumen for sliding over and receiving a separate medical guidewire and being insertable in a leading direction into a body of the patient, the proximal portion having a main section extending proximally from the distal sleeve and a distal transition extending distally from the main section, wherein the distal transition is fixedly coupled to an outer surface of the distal sleeve, the proximal portion comprises a communication channel for communicating a signal from the sensor to a location outside of the patient, and the proximal portion is adapted to facilitate positioning of the sensor within an anatomical structure of the patient.

2. The method of claim 1, wherein the first blood pressure is measured with the hemodynamic transducer.

3. The method of claim 1, wherein the first blood pressure is measured with the sensor.

4. The method of claim 1, wherein the sensor is carried by the distal sleeve.

5. The method of claim 1, wherein the sensor is carried by the proximal portion.

6. The method of claim 1, wherein the sensor comprises a first sensor and a second sensor, the first blood pressure is measured by the first sensor so as to generate a first signal, and the second blood pressure is measured by the second sensor so as to generate a second signal.

7. The method of claim 6, wherein the first sensor is carried by the distal sleeve and the second sensor is carried by the proximal portion.

8. The method of claim 6, wherein the second sensor is mounted a fixed distance from the first sensor.

9. The method of claim 1, further including providing a fluid injector system having the processor, the processor adapted to receive a first signal representative of the first blood pressure and a second signal representative of the second blood pressure and calculate the FFR based on the first and second signal.

10. The method of claim 1, further comprising making a therapy decision based on the calculated FFR being below a threshold value.

11. The method of claim 10, wherein the therapy decision comprises selecting an interventional therapy if the calculated FFR is less than about 0.75.

12. The method of claim 1, wherein the first blood pressure and second blood pressure are measured substantially simultaneously.

13. The method of claim 1, wherein the sensor is a Fabry-Perot fiber optic pressure sensor.

14. The method of claim 1, wherein the sensor is a piezoresistive pressure sensor.

15. The method of claim 1, wherein the sensor is a capacitive pressure sensor.

* * * * *